United States Patent
Mao et al.

(10) Patent No.: US 9,682,057 B2
(45) Date of Patent: Jun. 20, 2017

(54) CRYSTALLINE FORMS OF (N,N-DIETHYLCARBAMOYL)METHYL METHYL (2E)BUT-2-ENE-1,4-DIOATE, METHODS OF SYNTHESIS AND USE

(71) Applicant: XenoPort, Inc., Redwood City, CA (US)

(72) Inventors: Chen Mao, Foster City, CA (US); Randall A. Scheuerman, Santa Clara, CA (US); Sami Karaborni, Cupertino, CA (US)

(73) Assignee: XENOPORT, INC., Redwood City, CA (US)

( * ) Notice: Subject to any disclaimer, the term of this patent is extended or adjusted under 35 U.S.C. 154(b) by 0 days.

(21) Appl. No.: 15/214,563

(22) Filed: Jul. 20, 2016

(65) Prior Publication Data

US 2017/0042853 A1    Feb. 16, 2017

Related U.S. Application Data

(63) Continuation of application No. 14/478,627, filed on Sep. 5, 2014, now Pat. No. 9,416,096.

(60) Provisional application No. 61/874,758, filed on Sep. 6, 2013.

(51) Int. Cl.
*C07C 235/06* (2006.01)
*A61K 31/225* (2006.01)

(52) U.S. Cl.
CPC .................................. *A61K 31/225* (2013.01)

(58) Field of Classification Search
None
See application file for complete search history.

(56) References Cited

U.S. PATENT DOCUMENTS

| | | | |
|---|---|---|---|
| 3,139,395 A | 6/1964 | Griffin | |
| 3,336,364 A | 8/1967 | Dill | |
| 4,851,439 A | 7/1989 | Speiser et al. | |
| 4,863,916 A | 9/1989 | Habich et al. | |
| 4,959,389 A | 9/1990 | Speiser et al. | |
| 5,073,641 A | 12/1991 | Bundgaard et al. | |
| 5,145,684 A | 9/1992 | Liversidge et al. | |
| 5,149,695 A | 9/1992 | Speiser et al. | |
| 5,424,332 A | 6/1995 | Speiser et al. | |
| 5,451,667 A | 9/1995 | Speiser et al. | |
| 5,534,250 A | 7/1996 | Klaveness et al. | |
| 6,130,248 A | 10/2000 | Nudelman et al. | |
| 6,277,882 B1 | 8/2001 | Joshi et al. | |
| 6,355,676 B1 | 3/2002 | Joshi et al. | |
| 6,359,003 B1 | 3/2002 | Joshi et al. | |
| 6,379,697 B1 | 4/2002 | Gregoriadis et al. | |
| 6,436,992 B1 | 8/2002 | Joshi et al. | |
| 6,509,376 B1 | 1/2003 | Joshi et al. | |
| 6,613,800 B1 | 9/2003 | Smith | |
| 6,709,868 B2 | 3/2004 | Law et al. | |
| 6,723,508 B2 | 4/2004 | Sprenger et al. | |
| 6,858,750 B2 | 2/2005 | Joshi et al. | |
| 7,157,423 B2 | 1/2007 | Joshi et al. | |
| 7,320,999 B2 | 1/2008 | Joshi et al. | |
| 7,432,240 B2 | 10/2008 | Joshi et al. | |
| 7,612,110 B2 | 11/2009 | Joshi et al. | |
| 7,619,001 B2 | 11/2009 | Joshi et al. | |
| 7,638,118 B2 | 12/2009 | Flachsmann et al. | |
| 7,790,916 B2 | 9/2010 | Joshi et al. | |
| 7,803,840 B2 | 9/2010 | Joshi et al. | |
| 7,906,659 B2 | 3/2011 | Joshi et al. | |
| 7,915,310 B2 | 3/2011 | Joshi et al. | |
| 8,067,467 B2 | 11/2011 | Joshi et al. | |
| 8,148,414 B2 | 4/2012 | Gangakhedkar et al. | |
| 8,399,514 B2 | 3/2013 | Lukashev et al. | |
| 8,524,773 B2 | 9/2013 | Joshi et al. | |
| 8,669,281 B1 | 3/2014 | Zeidan et al. | |
| 8,759,393 B2 | 6/2014 | Joshi et al. | |
| 8,778,991 B2 | 7/2014 | Gangakhedkar et al. | |
| 8,785,443 B2 | 7/2014 | Gangakhedkar et al. | |
| 8,906,420 B2 | 12/2014 | Nilsson et al. | |
| 8,952,006 B2 | 2/2015 | Cundy et al. | |
| 9,416,096 B2 | 8/2016 | Mao et al. | |
| 2003/0018072 A1 | 1/2003 | Joshi et al. | |
| 2004/0054001 A1 | 3/2004 | Joshi et al. | |
| 2004/0102525 A1 | 5/2004 | Kozachuk | |
| 2005/0095292 A1 | 5/2005 | Benjamin et al. | |
| 2005/0096369 A1 | 5/2005 | Hoang | |
| 2005/0101779 A1 | 5/2005 | Sagi et al. | |
| 2005/0112193 A1 | 5/2005 | Phillips et al. | |
| 2005/0148664 A1 | 7/2005 | Joshi et al. | |
| 2005/0208133 A1 | 9/2005 | Tsutsumi et al. | |
| 2006/0205659 A1 | 9/2006 | Joshi et al. | |
| 2006/0269925 A1 | 11/2006 | Nunes et al. | |

(Continued)

FOREIGN PATENT DOCUMENTS

CN    1616400    5/2005
CN    101318901    12/2008

(Continued)

OTHER PUBLICATIONS

Altmeyer et al., Antipsoriatic effect of fumaric acid derivatives, J. Amer. Acad. Derm. (1994), 30(6): 977-981.

Altschul et al., "Gapped BLAST and PSI-BLAST: a new generation of protein database search programs," Nucleic Acids Research, 1997, vol. 25, No. 17, pp. 3389-3402.

Ashe, Learning and memory in transgenic mice modeling Alzheimer's . disease. Learning & Memory (2001), 8, 301-308.

(Continued)

*Primary Examiner* — Timothy R Rozof

(74) *Attorney, Agent, or Firm* — King & Spalding LLP

(57) ABSTRACT

Disclosed herein are crystalline forms of (N,N-Diethylcarbamoyl)methyl methyl (2E)but-2-ene-1,4-dioate, which is a prodrug of methyl hydrogen fumarate. Crystalline form 1, Crystalline form 2, Crystalline 3, and Crystalline form 4 are disclosed.

11 Claims, 12 Drawing Sheets

(56) References Cited

U.S. PATENT DOCUMENTS

| | | |
|---|---|---|
| 2007/0009475 A1 | 1/2007 | Flachsmann et al. |
| 2007/0027076 A1 | 2/2007 | Joshi et al. |
| 2007/0213300 A1 | 9/2007 | Liu et al. |
| 2007/0231382 A1 | 10/2007 | Karnachi et al. |
| 2007/0248663 A1 | 10/2007 | Joshi et al. |
| 2007/0253902 A1 | 11/2007 | Lobb et al. |
| 2008/0004344 A1 | 1/2008 | Nilsson et al. |
| 2008/0033199 A1 | 2/2008 | Lai et al. |
| 2008/0089861 A1 | 4/2008 | Went et al. |
| 2008/0089896 A1 | 4/2008 | Wang et al. |
| 2008/0227847 A1 | 9/2008 | Nilsson et al. |
| 2008/0233185 A1 | 9/2008 | Joshi et al. |
| 2008/0299196 A1 | 12/2008 | Nilsson et al. |
| 2008/0300217 A1 | 12/2008 | Nilsson |
| 2009/0011986 A1 | 1/2009 | Joshi et al. |
| 2009/0181085 A1 | 7/2009 | Joshi et al. |
| 2009/0182047 A1 | 7/2009 | Joshi et al. |
| 2009/0304790 A1 | 12/2009 | Nilsson et al. |
| 2010/0048651 A1 | 2/2010 | Gangakhedkar et al. |
| 2010/0099907 A1 | 4/2010 | Raillard et al. |
| 2010/0105784 A1 | 4/2010 | Remon et al. |
| 2010/0130607 A1 | 5/2010 | Gold |
| 2010/0144651 A1 | 6/2010 | Nilsson et al. |
| 2010/0226981 A1 | 9/2010 | Karaborni et al. |
| 2010/0247642 A1 | 9/2010 | Wu et al. |
| 2010/0260755 A1 | 10/2010 | Gammans et al. |
| 2011/0112196 A1 | 5/2011 | Lukashev |
| 2011/0124615 A1 | 5/2011 | Joshi et al. |
| 2011/0212169 A1 | 9/2011 | Bae et al. |
| 2011/0293711 A1 | 12/2011 | Joshi et al. |
| 2012/0034274 A1 | 2/2012 | Nilsson et al. |
| 2012/0034303 A1 | 2/2012 | Nilsson et al. |
| 2012/0095003 A1 | 4/2012 | Gangakhedkar et al. |
| 2012/0157523 A1 | 6/2012 | Gangakhedkar et al. |
| 2012/0165404 A1 | 6/2012 | Lukashev |
| 2013/0065909 A1 | 3/2013 | Milne et al. |
| 2013/0172391 A1 | 7/2013 | Kahrs |
| 2013/0203753 A1 | 8/2013 | Cundy et al. |
| 2013/0259856 A1 | 10/2013 | Kaye |
| 2013/0259906 A1 | 10/2013 | Joshi et al. |
| 2013/0295169 A1 | 11/2013 | Goldman et al. |
| 2013/0302410 A1 | 11/2013 | Gold |
| 2013/0317103 A1 | 11/2013 | Lukashev |
| 2013/0324539 A1 | 12/2013 | Virsik et al. |
| 2014/0051705 A1 | 2/2014 | Cundy et al. |
| 2014/0056973 A1 | 2/2014 | Ma et al. |
| 2014/0056978 A1 | 2/2014 | Karaborni et al. |
| 2014/0057917 A1 | 2/2014 | Cundy et al. |
| 2014/0057918 A1 | 2/2014 | Wustrow et al. |
| 2014/0065211 A1 | 3/2014 | Karaborni et al. |
| 2014/0066505 A1 | 3/2014 | Joshi et al. |
| 2014/0099364 A2 | 4/2014 | Nilsson et al. |
| 2014/0163100 A1 | 6/2014 | Dawson et al. |
| 2014/0179778 A1 | 6/2014 | Mao et al. |
| 2014/0179779 A1 | 6/2014 | Chao |
| 2014/0193386 A1 | 7/2014 | Preiss-Bloom et al. |
| 2014/0193387 A1 | 7/2014 | Gruskin et al. |
| 2014/0193388 A1 | 7/2014 | Velders et al. |
| 2014/0193390 A1 | 7/2014 | Valenzano et al. |
| 2014/0193392 A1 | 7/2014 | Annunziata et al. |
| 2014/0193393 A1 | 7/2014 | Gulati |
| 2014/0193495 A1 | 7/2014 | Nilsson |
| 2014/0194427 A1 | 7/2014 | Chao |
| 2014/0200272 A1 | 7/2014 | Nilsson et al. |
| 2014/0200273 A1 | 7/2014 | Nilsson et al. |
| 2014/0200363 A1 | 7/2014 | Guzowski et al. |
| 2014/0205659 A1 | 7/2014 | Nilsson et al. |
| 2014/0275048 A1 | 9/2014 | Zeidan et al. |
| 2014/0275250 A1 | 9/2014 | Cundy et al. |
| 2014/0284245 A1 | 9/2014 | Karaborni et al. |
| 2014/0323570 A1 | 10/2014 | Gold |
| 2014/0329818 A1 | 11/2014 | Gangakhedkar et al. |
| 2014/0336151 A1 | 11/2014 | Chao |
| 2014/0364604 A1 | 12/2014 | Raillard et al. |
| 2014/0378542 A1 | 12/2014 | Mao et al. |
| 2015/0038499 A1 | 2/2015 | Virsik |
| 2015/0073049 A1 | 3/2015 | Mao et al. |
| 2015/0079180 A1 | 3/2015 | Karaborni et al. |
| 2015/0190360 A1 | 7/2015 | Cundy |
| 2015/0265707 A1 | 9/2015 | Manthati et al. |
| 2016/0113879 A1 | 4/2016 | Karaborni et al. |

FOREIGN PATENT DOCUMENTS

| | | |
|---|---|---|
| CN | 101774913 A | 7/2010 |
| DE | 1165586 | 3/1964 |
| DE | 10360869 A1 | 4/2005 |
| EP | 2692344 A1 | 2/2014 |
| GB | 1153927 A | 6/1969 |
| GB | 1404989 A | 9/1975 |
| GB | 2285805 A | 7/1995 |
| JP | S60181047 | 9/1985 |
| JP | H03294245 | 12/1991 |
| JP | 2001158760 | 6/2001 |
| JP | 2002-027998 A | 1/2002 |
| PL | 153592 | 10/1991 |
| WO | WO 96/36613 | 11/1996 |
| WO | WO 98/29114 | 7/1998 |
| WO | WO 98/52549 | 11/1998 |
| WO | WO 98/53803 | 12/1998 |
| WO | WO 99/21559 | 5/1999 |
| WO | WO 99/49858 | 10/1999 |
| WO | WO 99/51191 A1 | 10/1999 |
| WO | WO 99/62973 A1 | 12/1999 |
| WO | WO 00/10560 A1 | 3/2000 |
| WO | WO 00/12072 A2 | 3/2000 |
| WO | WO 02/055063 | 7/2002 |
| WO | WO 02/055066 | 7/2002 |
| WO | WO 02/055067 | 7/2002 |
| WO | WO 03/087174 | 10/2003 |
| WO | WO 2005/023241 | 3/2005 |
| WO | WO 2005/027899 | 3/2005 |
| WO | WO 2006/037342 | 4/2006 |
| WO | WO 2006/050730 | 5/2006 |
| WO | WO 2006/122652 | 11/2006 |
| WO | WO 2007/006307 | 1/2007 |
| WO | WO 2007/006308 | 1/2007 |
| WO | WO 2007/042034 | 4/2007 |
| WO | WO 2007/042035 | 4/2007 |
| WO | WO 2008/096271 | 8/2008 |
| WO | WO 2008/097596 | 8/2008 |
| WO | WO 2010/022177 | 2/2010 |
| WO | WO 2010/079221 | 7/2010 |
| WO | WO 2010/079222 | 7/2010 |
| WO | WO 2010/126605 | 11/2010 |
| WO | WO 2011/080344 | 7/2011 |
| WO | WO 2011/100589 | 8/2011 |
| WO | WO 2012/162669 | 11/2012 |
| WO | WO 2012/170923 | 12/2012 |
| WO | WO 2013/022882 | 2/2013 |
| WO | WO 2013/076216 | 5/2013 |
| WO | WO 2013/119677 | 8/2013 |
| WO | WO 2013/119791 | 8/2013 |
| WO | WO 2014/020156 | 2/2014 |
| WO | WO 2014/031894 | 2/2014 |
| WO | WO 2014/031897 | 2/2014 |
| WO | WO 2014/071371 | 5/2014 |
| WO | WO 2014/096425 | 6/2014 |
| WO | WO 2014/100728 | 6/2014 |
| WO | WO 2014/190056 | 11/2014 |
| WO | WO 2015/028472 | 3/2015 |
| WO | WO 2015/028473 | 3/2015 |

OTHER PUBLICATIONS

Associated Press; FDA mulls drug to slow late-stage Alzheimer's [online]; [retrieved on Sep. 24, 2003]; retrieved from the internet, <http://www.cnn.com/2003/HEALTH/conditions/09/24/alzheimers.drug.ap/index.html>; Sep. 24, 2003; 2 pages.

Atreya et al., "NF-κB in inflammatory bowel disease," Journal of Internal Medicine (2008), 263(6), pp. 591-596.

Author Unknown, BG 00012, BG 12/oral fumarate, FAG-201, second-generation fumarate derivative—Fumapharm/Biogen Idec, Drugs RD (2005), 6(4): 229-230.

(56) References Cited

OTHER PUBLICATIONS

Bar-Or et al., "Clinical efficacy of BG-12 (dimethyl fumarate) in patients with relapsing-remitting multiple sclerosis: subgroup analyses of the DEFINE study," J. Neurol, 2013, vol. 260, pp. 2297-2305.

Bardgett et al., NMDA receptor blockade and hippocampal neuronal loss impair fear conditioning and position habit reversal in C57B1/6 mice. Brain Res Bull (2003), 60, 131-142.

Barnes, "Mediators of chronic obstructive pulmonary disease," Pharmacological Reviews (2004), 56(4), pp. 515-548.

Behari et al., Baseline characteristics of a subpopulation of Indian patients enrolled in two phase 3 trials for oral BG-12 in relapsing-remitting multiple sclerosis, 62nd Ann Mtg. Amer. Acad. Neurol. (2010), poster, 2 pages.

Benoit et al., Etude Clinique de L'ester B-Morpholinoethylique de L'Acide Niflumique en Stomatologie Infantile, Rev. Odontostomatol Midi Fr. (1975), 4: 249-261.

Bertone, "Prevalence of Gastric Ulcers in Elite, Heavy Use Western Performance Horses," AAEP Proceedings (2000). 46: 256-259.

Bhagavathula et al., 7-Chloro-5-(4-hydroxyphenyl)-1-methyl-3-(naphthalen-2-ylmethyl)-4,5-dihydro-1H-benzo[b][1,4]diazepin-2(3H)-one (Bz-423), a benzodiazepine, suppresses keratinocyte proliferation and has antipsoriatic activity in the human skin-severe, combined immunodeficient mouse transplant model. J Pharmacol Expt'l Therapeutics (2008), 324(3), 938-947.

Blad, et al., "Biological and Pharmacological Roles of HCA Receptors", Advances in Pharmacology, 2011, 62: 219-250.

Blandini, et al., "Glutamate and Parkinson's disease," Molecular Neurobiology (1996), 12(1), pp. 73-94.

Boehncke, "Animal Models of T Cell-Mediated Skin Diseases, Chapter 12: The Psoriasis SCID Mouse Model: A Tool for Drug Discovery?" Ernst Schering Res Found Workshop 50, Zollner et al., eds. New York: Springer (2005) pp. 213-234.

Brewer, et al., "Fumaric acid esters in the management of severe psoriasis", Clinical Experimental Dermatology, 2007, 32: 246-249.

Brown et al., "Goodman & Gilman's The Pharmacological Basis of Therapeutics, Tenth Edition: Chapter 7, Muscarinic Receptor Agonists and Antagonists," A. Gilman, J. Hardman and L. Limbird, eds., Mc-Graw Hill Press, 2001, pp. 155-173.

Bruhn et al., "Concordance between enzyme activity and genotype of glutathione S-transferase theta (GSTT1)," Biochemical Pharmacology, 1998, vol. 56, pp. 1189-1193.

Bundgaard et al., Esters of N,N-Disubstituted 2-Hydroxyacetamides as a Novel Highly Biolabile Prodrug Type for Carboxylic Acid Agents, J. Med. Chem. (1987), 30(3): 451-454.

Bundgaard et al., Glycolamide esters as a novel biolabile prodrug type for non-steroidal anti-inflammatory carboxylic acid drugs, Int. J. Pharm. (1988) 43: 101-110.

Büyükcoskun, Central Effects of Glucagon-like Peptide-1 on Cold Restraint Stress-induced Gastric Mucosal Lesions, Turk J. Gastroenterol (2007), 18(3): 150-156.

Büyükcoskun, Role of Intracerebroventricular Vasopressin in the Development of Stress-Induced Gastric Lesions in Rats, Physiol. Res. (1999), 48: 451-455.

Caira, "Crystalline Polymorphism of Organic Compounds," Topics in Current Chemistry, Springer, Berlin, DE (1998), vol. 198, pp. 163-208.

Camandola et al., "NF-κB as a therapeutic target in neurodegenerative diseases," Expert Opinion Therapeutic Targets (2007), 11(2), pp. 123-132.

Capello, et al., "Marburg type and Balo's concentric sclerosis: Rare and acute variants of multiple sclerosis", Neurological Sciences 200411 IT, vol. 25, No. Suppl. 4, Nov. 2004, pp. S361-S363.

Cavarra et al., Effects of cigarette smoke in mice with different levels of α1-proteinase inhibitor and sensitivity to oxidants. Am J Respir Crit Care Med (2001), 164, 886-890.

Champion, et al., "Flushing and Flushing Syndromes, Rosacea and Perioral Dermatitis", Rook Wilkinson Ebling Textbook of Dermatology, 6th ed. vol. 3, Oxford, UK: Blackwell Scientific, 1998, pp. 2099-2104.

Chaudhary et al., "Enhancement of solubilization and bioavailability of poorly soluble drugs by physical and chemical modifications: A recent review," Journal of Advanced Pharmacy Education & Research (2012), 2(1), pp. 32-67.

Chen et al., "Nanonization strategies for poorly water-soluble drugs," Drug Discovery Today, 2010, pp. 1-7.

Cockcroft et al., Bronchial reactivity to inhaled histamine: a method and clinical survey. Clin Allergy (1977), 7, 235-243.

Cross, et al. Dimethyl Fumarate, an Immune Modulator and Inducer of the Antioxidant Response, Suppresses HIV Replication and Macrophage-Mediated Mediated Neurotoxicity: A Novel Candidate for HIV Neuroprotection. The Journal of Immunology, (2011), 187(10): 5015-5025.

D'Acquisto et al., Inhibition of nuclear factor kappa B (NF-κB): an emerging theme in anti-inflammatory therapies. Molecular Interventions (2002), 2(1), 22-35.

Damasio; "Alzheimer's Disease and Related Dementias;" Cecil Textbook of Medicine; 1996; 20th Edition, vol. 2; pp. 1992-1996.

Dawson et al., "Bioequivalence of BG-12 (Dimethyl Fumarate) Administered as a Single 240 mg Capsule and Two 120 mg Capsules: Findings from a Randomized, Two-period Crossover Study", Poster P913 presented at the 28th Congress of the European Committee for Treatment and Research in Multiple Sclerosis, Oct. 10-13, 2012, Lyon France, 1 page.

De Jong et al., Selective stimulation of T helper 2 cytokine responses by the anti-psoriasis agent monomethylfunarate, Eur. J. Immunol. (1996), 26: 2067-2074.

Dibbert, et al.,: "Detection of fumarate-glutathione adducts in the portal vein blood of rats: Evidence for rapid dimethyl fumarate metabolism", Archives of Dermatological Research 2013 Springer Verlag DEU, vol. 305, No. 5, Jul. 2013 (Jul. 2013), pp. 477-451.

Dymicky, Preparation of Monomethyl Fumarate, Organic Preparations and Procedures International, vol. 15 No. 4 (1983), pp. 233-238.

Eberle, et al. Fumaric Acid Esters in Severe Ulcerative Necrobiosis Lipoidica: A Case Report and Evaluation of Current Therapies. Acta Dermato-Venereologica (2010) 90(1): 104-106.

Ellrichmann et al., Efficacy of fumaric acid esters in the R6/2 and YAC128 models of Huntington's disease, PLOS One (2011), 6(1): 11 pages.

Etter et al., "The Use of Cocrystallization as a Method of studying Hydrogen Bond Preferences of 2-Aminopyrimidine," Journal of the Chemical Society (1990), No. 8, pp. 589-591.

Etter et al., "Graph Set Analysis of Hydrobgen-Bond Patterns in Organic Crystals," Acta Crystallogr., Sect. B, Struct. Sci. (1990), B46, pp. 256-262.

Etter et al., "Hydrogen Bond Directed Cocrystallization and Molecular Recognition Properties of Diarylureas," Journal of the Chemical Society (1990), No. 112, pp. 8415-8426.

Eugster et al., Superantigen overcomes resistance of IL-6 deficient mice towards MOG-induced EAE by a TNFR1 controlled pathway. Eur J Immunol (2001), 31, 2302-2312.

European Commission Health & Consumer Protection Directorate-General, Report of the scientific committee on animal nutrition on the safety of fumaric acid, adopted Jan. 22, 2003: 18 pages.

Feinstein et al., Anti-inflammatory and prometabolic effects of BG-12 in glial cells, 26th Congress Eur. Cmtee. Treat. Res. Mult. Scler. (2010), poster: 1 page.

Fits et al., Imiquimod-Induced Psoriasis-Like Skin Inflammation in Mice Is Mediated via the IL-23/IL-17 Axis, J. Immunol. (2009), 182: 5836-5845.

Food and Drug Administration—Department of Health and Human Services; "International Conference on Harmonisation; Guidelines for the Photostability Testing of New Drug Substances and Products; Availability; Notice," Federal Register, vol. 62, No. 95; May 16, 1997, pp. 27115-27122.

Fox et al., Baseline characteristics of patients in a randomized, multicenter, placebo-controlled and active comparator trial evaluating efficacy and safety of BG-12 in relapsing-remitting multiple sclerosis: the CONFIRM trial, 62nd Ann Mtg. Amer. Acad. Neurol. (2010), poster, 2 pages.

(56) References Cited

OTHER PUBLICATIONS

Fox et al., Placebo-controlled phase 3 study of oral BG-12 or glatiramer in multiple sclerosis, N Engl J Med. Sep. 20, 2012;367(12):1087-97. Erratum in: N Engl J Med. Oct. 25, 2012;367(17):1673.

Frycak et al., Evidence of covalent interaction of fumaric acid esters with sulfhydryl groups in peptides, J. Mass. Spectrom. (2005), 40: 1309-1318.

Gadad et al., Synthesis, spectral studies and anti-inflammatory activity of glycolamide esters of niflumic acid as potential prodrugs, Arzneim Forsch Drug Res. (2002), 52(11): 817-821.

Gambichler, et al. Clearance of Necrobiosis lipoidica with Fumaric Acid Esters. Dermatology (2003), 207(4): 422-424.

Gesser et al., Dimethylfumarate specifically inhibits the mitogen and stress-activated kinases 1 and 2 (MSK1/2): Possible role for its anti-psoriatic effect. J Investigative Dermatology (2007), 127, 2129-2137.

Goke et al., Effect of a Specific Serine Protease Inhibitor on the Rat Pancreas: Systemic Administration of Camostate and Exocrine Pancreatic Secretion, Digestion (1984) 30: 171-178.

Gogas et al., Comparison of the efficacy and tolerability of a novel methyl hydrogen fumarate prodrug with dimethyl fumarate in rodent EAE and GI irritation models, XenoPort, Inc.; 26th Congress of the European Committee for Treatment and Research in Multiple Sclerosis (ECTRIMS), 2010 (Poster #671), 1 page.

Gold et al., Baseline characteristics of patients in the DEFINE trial: a randomized, multicenter, double blind, placebo-controlled, phase 3 study of BG-12 in relapsing-remitting multiple sclerosis, 62nd Ann Mtg. Amer. Acad. Neurol. (2010), poster, 2 pages.

Gold et al., Placebo-controlled phase 3 study of oral BG-12 for relapsing multiple sclerosis, N Engl J Med. Sep. 20, 2012;367(12):1098-107, Erratum in: N Engl J Med. Dec. 13, 2012;367(24):2362.

Gorbitz et al., "On the inclusion of solvent molecules in the crystal structures of organic compounds," Acta Cryst. (2000), B56, pp. 526-534.

Ghoreschi Kamran, et al., "Furmarates improve psoriasis and multiple sclerosis by inducing type II dendritic cells", The Journal of Experimental Medicine, Rockefeller University Press, US, vol. 208, No. 11, Oct. 24, 2011 (Oct. 24, 2011), pp. 2291-2303.

Griffin, et al., The Chemistry of Photodimers of Maleic and Fumaric Acid Derivatives. I. Dimethyl Fumarate Dimer; J. Am. Chem. Soc. (1961), 83: pp. 2725-2728.

Grigorian et al., Control of T-cell mediated autoimmunity by metabolite flux to N-glycan biosynthesis, J. Bio. Chem. (2007), 282(27): 20027-20035.

Guenther, et al., Macular Exanthema Due to Fumaric Acid Esters. Annals of Pharmacotherapy (2003), 37(2): 234-236.

Gurney et al., Motor neuron degeneration in mice that express a human Cu,Zn superoxide dismutase mutation. Science (1994), 264, 1772-1775.

Hanson et al., Nicotinic acid- and monomethyl funarate-induced flushing involves GPR109A expressed by keratinocytes and COX-2-dependent prostanoid formation in mice, J. Clin. Invest. (2010), 120(8): 2910-2919.

Heiligenhaus, et al. Influence of dimethylfumarate on experimental HSV-1 necrotizing keratitis. Graefe's Archive for Clinical and Experimental Ophthalmology (2004), 242(10): 870-877.

Heiligenhaus, et al. Improvement of herpetic stromal keratitis with fumaric acid derivate is associated with systemic induction of T helper 2 cytokines. Clinical and Experimental Immunology (2011), 142(1): 180-187.

Hiraku et al., Absorption and Excretion of Camostat Orally Administered to Male Rabbit and Healthy Subject, Iyakuhin Kenkyu (1982) 13(3): 756-765.

Hoefnagel, et al., "Long-term safety aspects of systemic therapy with fumaric acid esters in severe psoriasis", British Journal of Dermatology, 2003, 149: 363-369.

Horig et al., From bench to clinic and back: Perspective on the 1st IQPC Translational Research Conference, J. Transl. Med. (2004), 2(44), 8 pages.

Hoxtermann et al., Fumaric acid esters suppress peripheral CD4- and CD8-positive lymphocytes in psoriasis, Dermatology (1998), 196: 223-230.

Hurd et al., Vinylation and the Formation of Acylals:, J. Am. Chem. Soc.; vol. 78; Jan. 5, 1956; pp. 104-106.

Iyer et al., Synthesis of iodoalkylacylates and their use in the preparation of S-alkyl phosphorothiolates. Synth Commun (1995), 25(18), 2739-2749.

Jamil, et al., "Studies of Photostability of Reserpine in Parenteral Solutions," Die Pharmazie (1983), 38: pp. 467-469.

Jennings, Squamous cell carcinoma as a complication of fumaric acid ester immunosuppression, J. Eur. Acad. Dermatol. Venereol. (2009), DOI: 10.1111/j.1468-3083.2009.03234.x, 1 page.

Jurjus et al., Animal models of inflammatory bowel disease. J Pharmacol Toxicol Methods (2004), 50, 81-92.

Kappos et al., Efficacy and safety of oral fumarate in patients relapsing-remitting multiple sclerosis: a multicentre, randomised, double-blind, placebo controlled phase IIb study, Lancet (2008), 372: 1463-1472.

Kamimura et al., "Stereoselective formation of optically active 2-oxy-1,3-oxazolidin-4-ones from chiral O-acylmandelamides or lactamides", Tetrahedron 58, 2002, 8763-8770.

Khan et al., Synthesis and biological evaluation of glycolamide esters as potential prodrugs of some non-steroidal anti-inflammatory drugs, Ind. J. Chem. (2002) 41B: 2172-2175.

Killestein, et al., "Oral treatment for multiple sclerosis," Lancet Neurology, Lancet Publishing Group, London, GB, vol. 10, No. 11, Nov. 2011, pp. 1026-1034.

Klein, et al. Off-label use of fumarate therapy for granulomatous and inflammatory skin diseases other than psoriasis vulgaris: a retrospective study. (2012), Journal of the European Academy of Dermatology and venereology (2012), 26(11): 1400-1406 (also on-line ref: Klein, et al., (2011), J Eur Acad Dermatol Venereol doi: 10.1111/j.1468-3083.2011.04303.x).

Kreuter et al., Fumaric acid esters in necrobiosis lipoidica: results of a prospective noncontrolled study. British Journal of Dermatology (2005).

Kumar et al., "Molecular Complexes of Some Mono- and Dicarboxylic Acids with trans-1,4-Dithiane-1,4-dioxide," American Chemical Society, Crystal Growth & Design (2002), 2(4), pp. 313-318.

Layzer; "Section Five—Degenerative Diseases of the Nervous System"; Cecil Textbook of Medicine; 1996; 20th Edition, vol. 2; pp. 2050-2057.

Lee et al., Spotlight on fumarates, Int. MS J. (2008), 15: 12-18.

Lehmann et al., Fumaric acid esters are potent immunosuppressants: inhibition of acute and chronic rejection in rat kidney transplantation models by methyl hydrogen fumarate. Arch Dermatol Res (2002), 294, 399-404.

Lehmann et al., Dimethylfumarate induces immunosuppression via glutathione depletion and subsequent induction of heme oxygenase 1. J Investigative Dermatology (2007), 127, 835-845.

Lei et al., "Novel Technology of Dimethyl Fumarate Synthesis," Ziyuan Kaifa Yu Shichang (2011), 27(9), pp. 787-789.

Linker et al., Identification and development of new therapeutics for multiple sclerosis, Treds. Pharm. Sci. (2008), DOI 10.1016/j.tips.2008.07.012, 8 pages.

Linker et al., Fumaric acid esters exert neuroprotective effects in neuroinflammation via activation of the Nrf2 antioxidant pathway, Brain (2011), 134: 678-692.

Litjens e al., Monomethylfumarate affects polarization of monocyte-derived dendritic cells resulting in down-regulated Th1 lymphocyte responses, Eur. J. Immunol. (2004), 34: 565-575.

Litjens et al., Pharmacokinetics of oral fumarates in healthy subjects, Br. J. Clin. Pharmacol. (2004), 58(4): 429-432.

Litjens et al., Effects of monomethylfumarate on dendritic cell differentiation, Br. J. Dermatol. (2006), 154: 211-217.

Loewe et al., "Dimethylfumarate inhibits TNF-induced nuclear entry of NF-κB/p65 in human endothelial cells," The Journal of Immunology (2002), 168, pp. 4781-4787.

(56) References Cited

OTHER PUBLICATIONS

Loewe et al., Dimethylfumarate impairs melanoma growth in metastasis, Cancer Res. (2006), 66(24): 11888-11896.

Lopez-Diego et al., Novel therapeutic strategies for multiple sclerosis—a multifaceted adversary, Nat. Review. Drug Disc. (2008), 7:909-925.

Los et al., Nuevos Estered De Acidos Anilinonicotinicos Y N-Fenilantranilicos Sustituidos, II Farmaco—Ed. Sc. (1980), 36(5): 372-85.

Lukashev et al., Activation of Nrf2 and modulation of disease by BG00012 (dimethyl fumarate) suggest a dual cytoprotective and anti-inflammatory mechanism of action, 62nd Ann Mtg. Amer. Acad. Neurol. (2010), poster, 4 pages.

Mandhane, et al., Adenosine A2 receptors modulate haloperidol-induced catalepsy in rats. Eur. J. Pharmacol (1997), 328, 135-141.

Martin, "Molecular basis of the neurodegenerative disorders," The New England Journal of Medicine (1999), 340(25), pp. 1970-1980.

Martorana et al., Roflumilast fully prevents emphysema in mice chronically exposed to cigarette smoke. Am J Respir Crit Care Med (2005), 172, 848-853.

Meissner et al., "Dimethyl fumarate—only an anti-psoriatic medication?", Journal Der Deutschen Demrmatologischen Gesellschaft (2012), vol. 10, pp. 793-801.

Menter et al., Guidelines of care for the management of psoriasis and psoriatic arthritis, J. Am. Acad. Dermatol. (2009), doi:10.1016/j.jaad.2009.03.027, 35 pages.

Merisko-Liversidge et al., "Nanosizing: a formulation approach for poorly-water-soluble compounds," European Journal of Pharmaceutical Sciences, 18 (2003), pp. 113-120.

Miller et al., Experimental Autoimmune Encephalomyelitis in the Mouse, Current Protocols in Immunology (2007), Supp. 78: 15.1.1-15.1.18.

Milo, et al., "Combination therapy in multiple sclerosis", Journal of Neuroimmunology, vol. 231, No. 1, 2011, pp. 23-31.

Mosmann et al., TH1 and TH2 cells: different patterns of lymphokine secretion lead to different functional properties, Ann. Rev. Immunol. (1989), 7: 145-73.

Mrowietz, et al., "Dimethylfumarate for psoriasis: more than a dietary curiosity," Trends in Molecular Medicine (2005), 11(1), pp. 43-48.

Mrowietz, et al., "Treatment of Psoriasis with Fumaric Acid Esters: Results of a prospective Multicenter Study," British Journal of Dermatology (1998), 138: 456-460.

Mrowietz et al., "Treatment of severe psoriasis with fumaric acid esters: scientific background and guidelines for therapeutic use," British Journal of Dermatology (1999), 141, pp. 424-429.

Mrowietz et al., Treatment of psoriasis with fumaric acid esters (Fumaderm®), JDDG (2007), DOI: 10.1111/j.1610-0387.2007.06346.x, 2 pages.

Muller et al., "High-performance liquid chromatography/fluorescence detection of S-methylglutathione formed by glutathione-S-transferase T1 in vitro," Arch Toxicol, 2001, vol. 74, pp. 760-767.

Murakami et al., Suppression of a dextran sodium sulfate-induced colitis in mice by zerumbone, a subtropical ginger sesquiterpene, and nimesulide: separately and in combination. Biochemical Pharmacol (2003), 66, 1253-1261.

Naldi et al., Psoriasis (chronic plaque), Clin. Evid. (2009), 1(1706): 50 pages.

Nelson, et al., Effect of Dietary Inducer Dimethylfumarate on Glutathione in Cultured Human Retinal Pigment Epithelial Cells. Investigative Ophthalmology and Visual Science (1999), 40(9): 1927-1935.

Neymotin et al., Neuroprotective effect of Nrf2/AFE activators, CDDO ethylamide and CDDO trifluoroethylamide, in a mouse model of amyotrophic lateral sclerosis, Free Rad. Bio. Med (2011), 51: 88-96.

Nibbering et al., Intracellular signalling by binding sites for the antipsoriatic agent monomethylfumarate on human granulocytes, Br. J. Dermatol. (1997), 137: 65-75.

Nielsen, et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, Apr. 1988, pp. 285-298.

Offermans, The nicotinic acid receptor GPR109A (HM74A or PUMA-G) as a new therapeutic agent, Trends Pharm. Sci. (2006), 27(7): 384-390.

O'Toole, et al., Treatment of Carcinoid Syndrome: A Prospective Crossover Evaluation of Lanreotide versus Octreotide in Terms of Efficacy, Patient Acceptability, and Tolerance, American Cancer Society, Feb. 15, 2000, 88(4), 770-776.

Panagiotou et al., "Form Nanoparticles via Controlled Crystallization," Chemical Engineering Progress; Oct. 2008, 104, 10, pp. 33-39.

Pathak et al., "Supercritical fluid technology for enhanced drug delivery," Expert Opin. Drug Deliv. (2005) 2(4):747-761.

Peeters et al., Fumaric acid therapy for psoriatic arthritis. A randomized, double-blind, placebo-controlled study, Br. J. Rheumatol. (1992), 31(7): 502-504.

Pemble et al., "Human glutathione S-transferase Theta (GSTT1): cDNA cloning and the characterization of a genetic polymorphism," Biochem. J., 1994, vol. 300, pp. 271-276.

Rantanen, the cause of the Chinese sofa/chair dermatitis epidemic is likely to be contact allergy to dimethylfumarate, a novel potent contact sensitizer, Br. J. Dermatol. (2008), 159: 218-221.

Reddingius, Bioanalysis and pharmacokinetics of fumarates in humans, Ph.D. dissertation ETH No. 12199, Swiss Fed. Inst. Tech. Zurich (1997), 82 pages.

Reich et al., Efficacy and safety of fumaric acid esters in the long-term treatment of psoriasis—a retrospective study (FUTURE), JDDG (2009), DOI: 10.1111/j.1610-0387.2009.07120.x, 8 pages.

Richman et al., Nicotinic acid receptor agonists differentially activate downstream effectors, J. Bio. Chem. (2007), 282(25): 18028-18036.

Roll et al., Use of fumaric acid esters in psoriasis, Indian J. Dermatol. Ven. Lep. (2007), 73: 133-137.

Rostami-Yazdi, et al., "Detection of Metabolites of Fumaric Acid Esters in Human Urine: Implications for their mode of action", Journal of Investigative Dermatology, 2008, pp. 1-3.

Rostami-Yazdi et al., Pharmacokinetics of antipsoriatic fumaric acid esters in psoriasis patients, Arch. Dermatol. Res. (2010), 302: 531-538.

Rowland et al., "Amyotrophic lateral sclerosis," The New England Journal of Medicine (2001), 344(22), pp. 1688-1700.

Rubant et al., Dimethylfumarate reduces leukocyte rolling in vivo through modulation of adhesion molecule expression, J. Invest. Dermatol. (2007), 128: 326-331.

Sawant et al., "Necessity of Establishing Chemical Integrity of Polymorphs of Drug Substance Using a Combination of NMR, HPLC, Elemental Analysis, and Solid-State Characterization Techniques: Case Studies," Organic Process Research & Development (2013), vol. 17, No. 3, pp. 519-532.

Schafer et al., "Failure is an option: learning from unsuccessful proof-of-concept trials", Drug Discovery Today, vol. 13, Nos. 21/22; Nov. 2008; pp. 913-916.

Schilling, et al., "Fumaric acid esters are effective in chronic experimental autoimmune encephalomyelitis and suppress macrophage infiltration", Clinical and Experimental Immunology, 2006, 145: pp. 101-107.

Schimrigk, et al., "Oral fumaric acid esters for the treatment of active multiple sclerosis: an open-label, baseline-controlled pilot study," European Journal of Neurology (2006), vol. 13, pp. 604-610.

Schmidt, et al., "Reactivity of dimethyl fumarate and methylhydrogen fumarate towards glutathione and N-acetyl-1-cysteine-Preparation of S-substituted thiosuccinic acid esters", Bioorganic & Medicinal Chemistry, Pergamon, GB, vol. 15, No. 1 Nov. 15, 2006 (Nov. 15, 2006), pp. 333-342.

Seder et al., Acquisition of lymphokine-producing phenotype by CD4+ T-cells, Ann. Rev. Immunol. (1994), 12: 635-73.

Shan et al., "The role of cocrystals in pharmaceutical science," Drug Discovery Today (2008), 13(9/10), pp. 440-446.

(56) References Cited

OTHER PUBLICATIONS

Sharma et al., Distal effect on mass spectral fragmentations of glycolamide esters of 6-methoxy-2-naphthylacetic acid (6-MNA) and the crystal structure of N,N'-dimethyl-glycolamide ester of 6-MNA, Ind. J. Chem. (2004) 43B: 1758-1764.
Sheikh, et al., "Safety Tolerability and Pharmacokinetics of BG-12 Administered with and without Aspirin, Key Findings from a Randomized, Double-blind, placebo-controlled trial in healthy volunteers", Poster P04.136 presented at the 64th Annual Meeting of the American Academy of Neurology, Apr. 21-28, 2012, New Orleans, LA, 1 page.
Soelberg Sorensen et al., Oral fumarate for relapsing-remitting multiple sclerosis, Lancet (2008), 372: 1447-1448.
Spatz, et al., Methyl Hydrogen Fumarate, Journal of Organic Chemistry, 1958, 23 (10), 1559-1560.
Spencer et al., Induction of glutathione transferases and NAD(P)H: quinone reductase by fumaric acid derivatives in rodent cells and tissues, Cancer Res. (1990), 50: 7871-7875.
Spencer, "Tecfidera: an approach for repurposing," Pharmaceutical Patent Analyst, 2014, vol. 3(2), pp. 183-198.
Sprenger et al., "Characterization of the glutathione S-transferase GSTT1 deletion: discrimination of all genotypes by polymerase chain reaction indicates a trimodular genotype-phenotype correlation," Pharmacogenetics, 2000, vol. 10, pp. 557-565.
Stoof et al., The antipsoriatic drug dimethylfumarate strongly suppresses chemokine production in human keratinocytes and peripheral blood mononuclear cells, Br. J. Dermatol. (2001), 144: 1114-1120.
Tabruyn et al., NF-κB: a new player in angiostatic therapy. Angiogenesis (2008), 11, 101-106.
Talath et al., Stability studies of some glycolamide ester prodrugs of niflumic acid in aqueous buffers and human plasma by HPLC with UV detection, Arz. Forsch Drug Res. (2006), 56(9): 631-639.
Talath et al., Synthesis, stability studies, anti-inflammatory activity and ulcerogenicity of morpholinoalkyl ester prodrugs of niflumic acid, Arz. Forsch Drug Res. (2006), 56(11): 744-752.
Tang et al., the psoriasis drug monomethylfumarate is a potent nicotinic acid receptor agonist, Biochem. Biophys. Res. Comm. (2008), doi:10.1016/j.bbrc.2008.08.041, 4 pages.
Thing et al., "Prolonged naproxen joint residence time after intra-articular injection of lipophilic solutions comprising a naproxen glycolamide ester prodrug in the rat", International Journal of Pharmaceutics 451; Apr. 2013; pp. 34-40.
Thomson et al., FK 506: a novel immunosuppressant for treatment of autoimmune disease: rationale and preliminary clinical experience at the University of Pittsburgh, Springer Semin. Immunopathol. (1993), 14(4): 323-344.
Tracey et al., "Tumor necrosis factor antagonist mechanisms of action: a comprehensive review," Pharmacology & Therapeutics (2008), 117, pp. 244-279.
Treumer et al., Dimethylfumarate is a potent inducer of apoptosis in human T cells. J Invest Dermatol (2003), 121, 1383-1388.
Van Schoor et al., Effect of inhaled fluticasone on bronchial responsiveness to neurokinin A in asthma. Eur Respir J (2002), 19, 997-1002.
Van Schoor et al., The effect of the NK2 tachykinin receptor antagonist SR 48968 (saredutant) on neurokinin A-induced bronchoconstriction in asthmatics, Eur Respir J (1998) 12: 17-23.
Vandermeeren et al., Dimethylfumarate is an inhibitor of cytokine-induced E-selectin, VCAM-1, and ICAM-1 expression in human endothelial cells. Biochem Biophys Res Commun (1997), 234, 19-23.
Villegas et al., A new flavonoid derivative, dosmalfate, attenuates the development of dextran sulphate sodium-induced colitis in mice. Int'l Immunopharmacol (2003), 3, 1731-1741.
Virley, "Developing therapeutics for the treatment of multiple sclerosis," NeuroRx: The Journal of the American Society for Experimental NeuroTherapeutics (2005), vol. 2, pp. 638-649.
Vishweshwar et al., "Pharmaceutical Co-Crystals," Journal of Pharmaceutical Sciences (2006), 95(3), pp. 499-516.
Wadhwa et al., Glycolamide esters of 6-methoxy-2-naphthylacetic acid as potential prodrugs—Synthetic and spectral studies, Ind. J. Chem. (1995), 34B: 408-415.
Wain et al., Treatment of severe, recalcitrant, chronic plaque psoriasis with fumaric acid esters: a prospective study, Br. J. Dermatol. (2009), DOI 10.1111/j.1365-2133.2009.09267.x, 8 pages.
Wakkee et al., "Drug evaluation: BG-12, an immunomodulary dimethylfumarate," Current Opinion in Investigational Drugs (2007), 8(11), pp. 955-962.
Wang, et al., Evidence-Based Treatment of Chronic Leg Ulcers in A Patient with Necrobiosis Lipoidica Deabeticorum. Chinese Journal of Evidence-Based Medicine (2007), 7(11): 830-835.
Weber et al., Synthesis, In Vitro Skin Permeation Studies, and PLS-Analysis of New Naproxen Derivatives, Pharm. Res. (2001) 18(5): 600-607.
Weber et al., Treatment of disseminated granuloma annulare with low-dose fumaric acid, Acta Derm. Venereol. (2009), 89: 295-298.
Werdenberg et al., Presystemic metabolism and intestinal absorption of antipsoriatic fumaric acid esters, Biopharm. Drug. Dispos. (2003), 24: 259-273.
Whiteley et al., Models of Inflammation: Measuring Gastrointestinal Ulceration in the Rat, Curr. Protocol. Pharm. (1998): 10.2.1-10.2.4.
Wingerchuk et al., "Multiple sclerosis: current pathophysiological concepts," Laboratory Investigation (2001), 81(3), pp. 263-281.
Winkler, et al., Oxidative damage and age-related macular degeneration. Molecular vision, (1999), 5:32, 11 pages.
Woodworth et al., Oral BG-12 in combination with interferon beta or glatiramer acetate: pharmacokinetics, safety and tolerability, 26th Congress Eur. Cmtee. Treat. Res. Mult. Scler. (2010), poster: 1 page.
Woodworth et al., "Pharmacokinetics of Oral BG-12 Alone Compared with BG-12 and Interferon B-1a or Glatiramer Acetate Administered Together, Studied in Healthy Volunteers", Poster P04.207 presented at the 62nd Annual Meeting of the American Academy of Neurology, Apr. 10-17, 2010, Toronto, Ontario, Canada, 2 pages.
Wu et al., "Regulatory perspectives of Type II prodrug development and time-dependent toxicity management: Nonclinical Pharm/Tox analysis and the role of comparative toxicology", Science Direct, Toxicology 236; Apr. 2007; pp. 1-6.
Wustrow et al., Comparison of the efficacy and tolerability of a novel methyl hydrogenfumarate prodrug with dimethylfumarate in rodent EAE and GI irritation models, XenoPort, Inc., Oct. 13-16, 2010, 1 page.
Xenoport, Inc., XenoPort announces presentation of preclinical data for novel fumarate analog XP23829 at ECTRIMS, Press Release dated Oct. 13, 2010, 3 pages.
Yamada et al., "Synthesis and Polymerization of Unsaturated Dibasic Acid Derivatives," Yuki Gosei Kagaku Kyokaishi (1965), 23(2), 19 pages.
Yang et al., Neuroprotective effects of the triterpenoid, CDDO methyl amide, a potent inducer of Nrf2-mediated transcription, PLOS One (2009), 4(6) doi:10.1371/journal.pone.0005757: 13 pages.
Yazdi et al., Fumaric acid esters. Clinics Dermatology (2008), 26, 522-526.
Zhang et al., "Synthesis of Dimethyl Fumarate with Orthogonal Test," Jingxi Huagong Zhongjianti (2006), 36(6), pp. 71-72.
Zhao et al., "Synthesis and antimicrobial active of monomethyl fumarate," Shipin Gongye Keji (2008), 29(6), pp. 259-262.
Zheng et al., "Improved Preparation of Monomethyl Fumarate," Huaxue Shijie (2004), 45(4), pp. 207-208, 217.
Zhu et al., Inhibition of dendritic cell differentiation by fumaric acid esters, J. Invest. Dermatol. (2001), 116: 203-208.
The Engineering Tool Box, "Acids—pH Values," <http://www.engineeringtoolbox.com/acids-ph-d_401.html>, published Feb. 24, 2006, pp. 1-2.
Steckel et al., "The extrusion and speronization of chitosan," Pharmaceutical Technology Europe, <http://www.pharmtech.com/extrusion-and-spheronization-chitosan>, published Jul. 2, 2007, pp. 1-12.
Mannervik et al., "Identification of three classes of cytosolic glutathione transferase common to several mammalian species:

(56) References Cited

OTHER PUBLICATIONS

Correlation between structural data and enzymatic properties," Proc. Natl. Acad. Sci., USA, Nov. 1985, vol. 82, pp. 7202-7206.
O'Donnell et al., "Remington The Science and Practice of Pharmacy" 21st Edition, 2005, Chapter 52, pp. 1025-1036.
Bhattacharya et al., Polymorphism in Pharmaceutical Solids: Thermoanalytical and Crystallographic Methods 334 (Brittain H. ed., 2d ed. Informa Healthcare USA, Inc. 2009) (1999), 20 pages.
Ivanisevic et al., "Uses of X-Ray Powder Diffraction in the Pharmaceutical Industry," Pharmaceutical Formulation & Quality, 32 (2011), pp. 30-33.
Gogas et al., "Comparison of the efficacy and tolerability of a novel methyl hydrogen fumarate prodrug with dimethyl fumarate in rodent EAE and GI irritation models," Multiple Sclerosis, 2010, vol. 16, No. 10 Supplement, pp. S230-S231.
Dow, "Methocel Cellulose Technical Handbook", <http://www.dow.com/dowwolff/en/pdf/192-01062.pdf>, 2002, 32 pages.
Carter et al., Chemotherapy of Cancer, 2nd ed., 1981, pp. 362-365.
General pharmaceutics (5th edition), 1997, 5 pages, published in Japan.
Tammara et al., "Morpholinoalkyl Ester Prodrugs of Diclofenac: Synthesis, In Vitro and In Vivo Evaluation," Journal of Pharmaceutical Sciences, 1994 vol. 83, No. 5, pp. 644-648.
General pharmaceutics (5th edition) with partial translation of pp. 208-209, 1997, 5 pages, published in Japan.
Compound (CAS RN 473669-27-1) entered STN chemical database on Nov. 15, 2002 by Ambinter, 4 pages.
Booth et al., "Regulation of dimethyl-fumarate toxicity by proteasome inhibitors," Cancer Biology & Therapy, Dec. 2014, vol. 15(12), pp. 1646-1657.
Silhavy et al., "Fumaric Acid Esters Can Block Pro-Inflammatory Actions of Human CRP and Ameliorate Metabolic Disturbances in Transgenic Spontaneously Hypertensive Rats," PLOS ONE, Jul. 2014, vol. 9, Issue 7, e101906, pp. 1-9.

CRYSTALLINE FORMS OF (N,N-DIETHYLCARBAMOYL)METHYL METHYL (2E)BUT-2-ENE-1,4-DIOATE, METHODS OF SYNTHESIS AND USE

CROSS-REFERENCE

This application is a continuation of U.S. patent application Ser. No. 14/478,627, filed Sep. 5, 2014, which claims the benefit of U.S. Provisional Application Ser. No. 61/874,758, filed Sep. 6, 2013, and entitled "CRYSTALLINE FORMS OF (N,N-DIETHYLCARBAMOYL)METHYL METHYL (2E)BUT-2-ENE-1,4-DIOATE, METHODS OF SYNTHESIS AND USE," the contents of which are hereby incorporated by reference in their entireties.

FIELD

Disclosed herein are novel crystalline forms of (N,N-Diethylcarbamoyl)methyl methyl (2E)but-2-ene-1,4-dioate.

BACKGROUND

In general, crystalline forms of drugs are utilized in dosage forms rather than amorphous forms of drugs, in part, because of their superior stability. For example, in many situations, an amorphous drug converts to a crystalline drug form upon storage. Because amorphous and crystalline forms of a drug typically have different physical properties, chemical properties, potencies and/or bioavailabilities, such interconversion is undesirable for safety reasons in pharmaceutical administration.

Polymorphs are crystals of the same molecule which have different physical properties because the crystal lattice contains a different arrangement of molecules. For example, certain polymorphs can include different hydration states that incorporate water into the crystalline structure without chemical alteration of the molecule itself. In that regard, certain compounds can exist in anhydrous and hydrated forms, where the hydrated forms can include, for example, hydrates, dihydrates, trihydrates, and the like, or partial hydrates such as hemihydrates. The different physical properties exhibited by polymorphs can affect important pharmaceutical parameters such as storage, stability, compressibility, density (which is important in formulation and product manufacturing) and dissolution rates (which are important in determining bioavailability). Stability differences may result from changes in chemical reactivity (e.g., differential hydrolysis or oxidation, such that a dosage form discolors more rapidly when the dosage form comprises one polymorph rather than another polymorph), mechanical changes (e.g., tablets crumble on storage as a kinetically favored crystalline form converts to a thermodynamically more stable crystalline form) or both (e.g., tablets of one polymorph are more susceptible to breakdown at high humidity). Solubility differences between polymorphs may, in extreme situations, result in transitions to crystalline forms that lack potency and/or are toxic. In addition, the physical properties of a particular crystalline form may be important in pharmaceutical processing. For example, one particular crystalline form may form solvates more readily or may be more difficult to filter and wash free of impurities than other forms (e.g., particle shape and size distribution might be different between one crystalline form relative to other forms).

Regulatory agencies such as the United States Food and Drug Administration closely regulate the polymorphic content of the active component of a drug in solid dosage forms. In general, regulatory agencies require batch-by-batch monitoring for polymorphic drugs if anything other than the pure, thermodynamically preferred polymorph is marketed. Accordingly, medical and commercial reasons favor synthesizing and marketing the most thermodynamically stable polymorph of a crystalline drug substance in solid drugs, which is substantially free of other, less favored polymorphs.

(N,N-Diethylcarbamoyl)methyl methyl (2E)but-2-ene-1,4-dioate (1) has the following chemical structure:

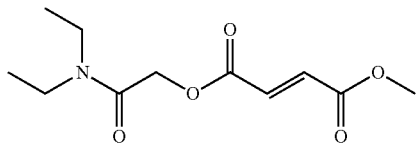 [SMILES: CCN(CC)C(=O)COC(=O)/C=C/C(=O)OC]

Compound (1) is a prodrug of methyl hydrogen fumarate. Once administered, the compound is metabolized in vivo into an active metabolite, namely, methyl hydrogen fumarate (MHF) which is also referred to herein as monomethyl fumarate (MMF). The in vivo metabolism of (N,N-Diethylcarbamoyl)methyl methyl (2E)but-2-ene-1,4-dioate to MHF/MMF is illustrated below:

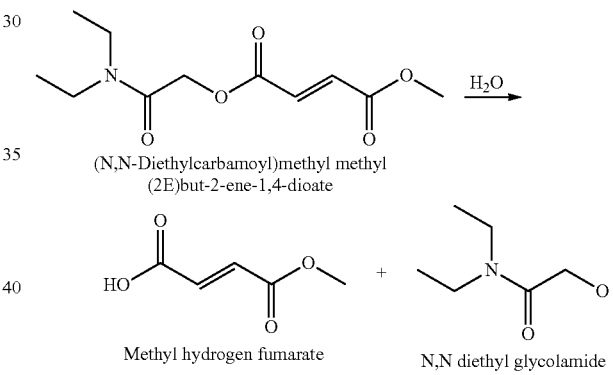

(N,N-Diethylcarbamoyl)methyl methyl (2E)but-2-ene-1,4-dioate

Methyl hydrogen fumarate     N,N diethyl glycolamide

Compound (1) is synthesized in Example 1 of Gangakhedkar et al. U.S. Pat. No. 8,148,414 and is disclosed as having a melting point between 53° C. and 56° C. Oral dosage forms comprising compound (1) are disclosed in U.S. patent application Ser. No. 13/973,456 filed Aug. 22, 2013, and Ser. No. 13/973,622 filed Aug. 22, 2013. High drug load formulations of compound (1) are disclosed in U.S. patent application Ser. No. 13/973,542 filed Aug. 22, 2013. Therapeutic uses and methods of treatment for compound (1) are disclosed in U.S. patent application Ser. No. 13/973,820 filed Aug. 22, 2013, Ser. No. 13/906,155 filed May 30, 2013, Ser. No. 13/973,700 filed Aug. 22, 2013, and Ser. No. 13/973,780 Aug. 22, 2013. Methods of making compound (1) are disclosed in U.S. patent application Ser. No. 14/298,713 filed Jun. 6, 2014. The contents of each of the above referenced patents and patent applications are hereby incorporated by reference in their entireties.

Co-crystalline forms of (N,N-Diethylcarbamoyl)methyl methyl (2E)but-2-ene-1,4-dioate with different co-formers are disclosed in U.S. patent application Ser. No. 14/072,138 filed Nov. 5, 2013, the contents of which is hereby incorporated by reference in its entirety.

SUMMARY

The present disclosure describes novel crystalline forms of (N,N-Diethylcarbamoyl)methyl methyl (2E)but-2-ene-1,4-dioate having improved physicochemical properties that may be used in pharmaceutical processing and in pharmaceutical compositions and therapeutic methods of treatment.

In a first aspect, a crystalline form 1 of (N,N-Diethylcarbamoyl)methyl methyl (2E)but-2-ene-1,4-dioate, pharmaceutical compositions comprising the form 1, and methods of administering the form 1 to a patient in need thereof for treating a disease, are provided.

In a second aspect, a crystalline form 2 of (N,N-Diethylcarbamoyl)methyl methyl (2E)but-2-ene-1,4-dioate, pharmaceutical compositions comprising the form 2, and methods of administering the form 2 to a patient in need thereof for treating a disease, are provided.

In a third aspect, a crystalline form 3 of (N,N-Diethylcarbamoyl)methyl methyl (2E)but-2-ene-1,4-dioate, pharmaceutical compositions comprising the form 3, and methods of administering the form 3 to a patient in need thereof for treating a disease, are provided.

In a fourth aspect, a crystalline form 4 of (N,N-Diethylcarbamoyl)methyl methyl (2E)but-2-ene-1,4-dioate, pharmaceutical compositions comprising the form 4, and methods of administering the form 4 to a patient in need thereof for treating a disease, are provided.

DEFINITIONS

Figure 1:
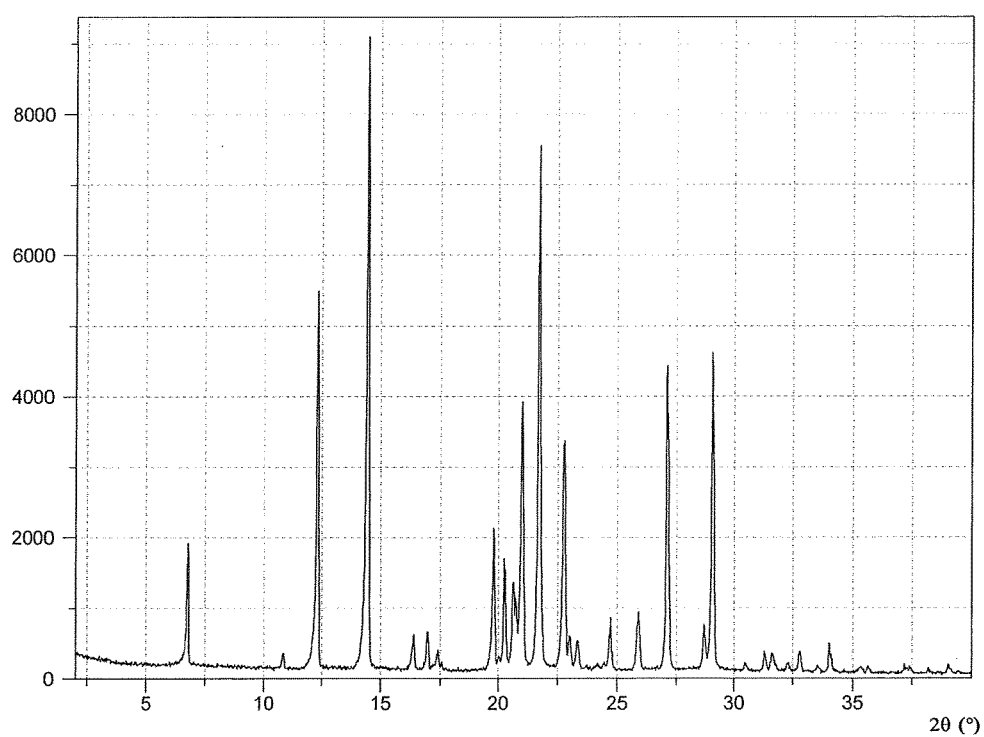
FIG. 1 is an X-ray powder diffractogram (XRPD) of a crystalline form 1 of (N,N-Diethylcarbamoyl)methyl methyl (2E)but-2-ene-1,4-dioate.

Unless defined otherwise, all technical and scientific terms used herein have the same meaning as is commonly understood by one of skill in the art to which the present disclosure belongs.

"Bioavailability" refers to the amount of a drug that reaches the systemic circulation of a patient following administration of the drug, or a prodrug thereof, to the patient and may be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or prodrug thereof to the patient, and $T_{max}$ is the time to the maximum concentration ($C_{max}$) of a drug in the plasma or blood of a patient following administration of a dose of the drug or prodrug thereof to the patient.

"Crystalline" means having a regularly repeating arrangement of molecules.

"Crystalline (N,N-Diethylcarbamoyl)methyl methyl (2E) but-2-ene-1,4-dioate" refers to a compound in which crystalline (N,N-Diethylcarbamoyl)methyl methyl (2E)but-2-ene-1,4-dioate is not associated with water molecules. Other chemical names for crystalline (N,N-Diethylcarbamoyl) methyl methyl (2E)but-2-ene-1,4-dioate include, without limitation, anhydrous crystalline (N,N-Diethylcarbamoyl) methyl methyl (2E)but-2-ene-1,4-dioate, crystalline polymorphic forms of (N,N-Diethylcarbamoyl)methyl methyl (2E)but-2-ene-1,4-dioate, crystalline forms and anhydrous crystalline polymorphic forms of (N,N-Diethylcarbamoyl) methyl methyl (2E)but-2-ene-1,4-dioate.

"Disease" refers to a disease, disorder, condition, symptom, or indication. This term is used interchangeably with the phrase "disease or disorder."

"Dosage form" refers to a form of a formulation that comprises an amount of active agent or a prodrug of an active agent, for example, the monomethyl fumarate prodrug (N,N-Diethylcarbamoyl)methyl methyl (2E)but-2-ene-1,4-dioate, which can be administered to a patient to achieve a therapeutic effect. An oral dosage form is intended to be administered to a patient via the mouth and swallowed. Examples of oral dosage forms include capsules, tablets, and liquid suspensions. A dose of a drug may include one or more dosage forms administered simultaneously or over a period of time.

"Patient" includes mammals, such as for example, humans.

"Pharmaceutical composition" refers to a composition comprising at least one compound provided by the present disclosure and at least one pharmaceutically acceptable vehicle with which the compound is administered to a patient.

"Pharmaceutically acceptable" refers to approved or approvable by a regulatory agency of a federal or a state government, listed in the U.S. Pharmacopeia, or listed in other generally recognized pharmacopeia for use in mammals, including humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing, with which crystalline forms of (N,N-Diethylcarbamoyl)methyl methyl (2E)but-2-ene-1,4-dioate can be administered to a patient, which does not destroy the pharmacological activity thereof, and which is nontoxic when administered in doses sufficient to provide a therapeutically effective amount of one or both of the compounds.

"Prodrug" refers to a derivative of an active compound (such as a drug) that undergoes a transformation under the conditions of use, such as within the body, to release the active compound or drug. Prodrugs are frequently, but not necessarily, pharmacologically inactive until converted into the active compound or drug. Prodrugs can be obtained by bonding a promoiety (defined herein), typically via a functional group, to a drug. For example, the monomethyl fumarate prodrug (N,N-Diethylcarbamoyl)methyl methyl (2E)but-2-ene-1,4-dioate is metabolized within a patient's body to form the parent drug monomethyl fumarate.

"Promoiety" refers to a group bonded to a drug, typically to a functional group of the drug, via one or more bonds that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach, or the agent may be supplied exogenously. For example, the promoiety of (N,N-Diethylcarbamoyl)methyl methyl (2E)but-2-ene-1,4-dioate is:

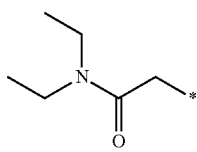 [SMILES: *CC(=O)N(CC)CC]

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. The actual amount required for treatment of any particular patient will depend upon a variety of factors including the disorder being treated and its severity; the specific pharmaceutical composition employed; the age, body weight, general health, sex and diet of the patient; the mode of administration; the time of administration; the route of administration; the rate of excretion of a disclosed crystalline form; the duration of the treatment; any drugs used in combination or coincidental with the specific compound employed; the discretion of the prescribing physician; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001. A therapeutically effective amount in any given instance can be readily ascertained by those skilled in the art and/or is capable of determination by routine experimentation.

The term "purity", when referring to one of the crystalline forms 1, 2, 3 and/or 4 of (N,N-Diethylcarbamoyl)methyl methyl (2E)but-2-ene-1,4-dioate disclosed herein, means the degree to which the particular crystalline form is undiluted or unmixed with another crystalline form and/or extraneous material(s), and is expressed as a percentage by weight (wt %). The term "purity", when referring to a formulation or dosage form of one of the crystalline forms 1, 2, 3 and/or 4 of (N,N-Diethylcarbamoyl)methyl methyl (2E)but-2-ene-1, 4-dioate disclosed herein, which formulation or dosage form comprises the particular crystalline form as the active pharmaceutical agent (as well as one or more other materials such as a pharmaceutically acceptable vehicle), means the degree to which the active pharmaceutical agent in the formulation or dosage form comprises that particular crystalline form and no other crystalline form(s) of (N,N-Diethylcarbamoyl)methyl methyl (2E)but-2-ene-1,4-dioate, and is also expressed as a percentage by weight (wt %). Since the weight percent of a particular crystalline form can vary with measurements taken by different instruments, different calibrations and/or different software packages, those skilled in the art will appreciate that any measured purity level will show some variability. Due to these sources of variability, it is common to recite purity using the word "about" or "at least" when referring to the percent purity of a crystalline form.

"Treating" or "treatment" of any disease or disorder refers to reversing, alleviating, arresting or ameliorating a disease or disorder, or at least one of the clinical symptoms of a disease or disorder, reducing the risk of acquiring at least one of the clinical symptoms of a disease or disorder, inhibiting the progress of a disease or disorder or at least one of the clinical symptoms of the disease or disorder, or reducing the risk of developing at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to protecting against or delaying the onset of at least one or more symptoms of a disease or disorder in a patient.

Reference is now made in detail to certain embodiments of crystalline forms, dosage forms and methods of use. The disclosed embodiments are not intended to be limiting of the claims. To the contrary, the claims are intended to cover all alternatives, modifications, and equivalents.

DETAILED DESCRIPTION

The present disclosure is directed to crystalline forms of (N,N-Diethylcarbamoyl)methyl methyl (2E)but-2-ene-1,4-dioate.

Four different crystalline forms of (N,N-Diethylcarbamoyl)methyl methyl (2E)but-2-ene-1,4-dioate are disclosed herein. The first form is form 1. The second form is form 2. The third form is form 3. The fourth form is form 4.

TABLE 1

| Crystalline Forms | Melting Point (° C.) |
|---|---|
| Form 1 | 58 |
| Form 2 | 50 |
| Form 3 | 47 |
| Form 4 | Unknown |

As can be seen from the data in Table 1, the form 1, form 2, and form 3 disclosed herein each exhibit a different melting point from each other.

Differential scanning calorimetry, or DSC, is a thermoanalytical technique in which the difference in the amount of heat required to increase the temperature of a sample and reference is measured as a function of temperature. DSC data shows differential heat flow plotted against temperature. As a sample undergoes a thermal event, it is effectively altering the heat flow due to the latent heat associated with the thermal event, which is then reflected as a peak or a shift in baseline. DSC can be used to characterize thermal properties of crystalline forms, such as melting temperature or heat of fusion. Therefore, the melting points of the crystalline form 1, form 2 and form 3 disclosed herein can be characterized by DSC. The crystalline form 4 can be characterized by having a DSC thermogram peak.

Single-crystal X-ray diffraction provides three-dimensional structural information about the positions of atoms and bonds in a crystalline form. It is not always possible or feasible, however, to obtain such a structure from a crystalline form due to, for example, insufficient crystal size or difficulty in preparing crystals of sufficient quality for single-crystal X-ray diffraction. Structural identification information can, however, be obtained from other solid-state techniques such as X-ray powder diffraction and Raman spectroscopy. These techniques are used to generate data on a solid crystalline form. Once that data has been collected on a known crystalline form, that data can be used to identify the presence of that crystalline form in other materials. Thus, these data effectively characterize the crystalline form. For example, an X-ray powder diffraction pattern, or a portion thereof, can serve as a fingerprint which characterizes a crystalline form.

An X-ray powder diffraction plot is an x-y graph with scattering angles 2θ (diffraction) on the x-axis and intensity on the y-axis. The peaks within this plot can be used to characterize a crystalline form. Although the peaks within an entire diffractogram can be used to characterize a crystalline form, a subset of the more characteristic peaks can also be used to accurately characterize a crystalline form. The data is often represented by the position of the peaks on the x-axis rather than the intensity of peaks on the y-axis because peak intensity may vary with sample orientation. There is also variability in the position of peaks on the x-axis. There are several sources of this variability, one of which comes from sample preparation. Samples of the same crystalline material prepared under different conditions may yield slightly different diffractograms. Factors such as particle size, moisture content, solvent content, and orientation can affect how a sample diffracts X-rays. Another source of variability comes from instrument parameters. Different X-ray instruments operate using different parameters and these may lead to slightly different diffraction patterns from the same crystalline form. Likewise, different software packages process X-ray data differently and this also leads to variability. These and other sources of variability are known to those of ordinary skill in the art. Due to these sources of variability, it is common to recite X-ray diffraction peaks using the word "about" prior to the peak value in 2θ. The word "about" incorporates this variability which under most sampling conditions, and most data collection and data processing conditions, leads to a variability in peak position of about plus or minus 0.2 scattering angle (2θ). Thus, when a peak is said to be at about 10.5 scattering angle (2θ), under most sampling, data collection, and data processing conditions, that peak will appear anywhere between 10.3 (2θ) and 10.7 (2θ). In characterizing the crystalline forms disclosed herein, the X-ray diffraction peaks were all measured using Cu—$K_\alpha$ radiation and all peaks herein cited refer to peaks diffracted from X-rays with that wavelength.

High-performance liquid chromatography, or HPLC, is a chromatographic technique used to separate the compounds in a mixture, to identify each compound, and to quantify each compound. HPLC is a technique known in the art to determine the purity of a compound. The purity of forms 1, 2, 3 and 4 of (N,N-Diethylcarbamoyl)methyl methyl (2E)but-2-ene-1,4-dioate can be determined using HPLC as is well known to those of ordinary skill in the art.

(N,N-Diethylcarbamoyl)methyl methyl (2E)but-2-ene-1,4-dioate: Form 1

One crystalline form disclosed herein is form 1 of (N,N-Diethylcarbamoyl)methyl methyl (2E)but-2-ene-1,4-dioate. Differential scanning calorimetry (DSC) analysis of form 1 shows a melting point between about 56° C. and about 60° C., in certain embodiments between about 57° C. and about 59° C., and in certain embodiments at about 58° C.

The purity of crystalline form 1 of (N,N-Diethylcarbamoyl)methyl methyl (2E)but-2-ene-1,4-dioate is at least 99 wt % as measured by HPLC. In certain embodiments the purity of crystalline form 1 is at least 99.5 wt % as measured by HPLC. In certain embodiments the purity of crystalline form 1 is at least 99.9 wt % as measured by HPLC.

FIG. 1 is an X-ray powder diffractogram (XRPD) of form 1 of the (N,N-Diethylcarbamoyl)methyl methyl (2E)but-2-ene-1,4-dioate showing the diffraction pattern measured using Cu—$K_\alpha$ radiation. Table 2 lists the approximate numerical values of the XRPD peak positions of the FIG. 1 diffractogram.

TABLE 2

XRPD Peaks for (N,N-Diethylcarbamoyl)methyl methyl (2E)but-2-ene-1,4-dioate: Form 1

| Pos. [°2Th.] | Height [cts] | FWHM [°2Th.] | d-spacing [Å] | Rel. Int. [%] |
|---|---|---|---|---|
| Peaks (5 Highest Peaks) | | | | |
| 14.4566 | 8669.85 | 0.0836 | 6.12715 | 100 |
| 21.7146 | 6282.16 | 0.1004 | 4.09281 | 72.46 |
| 12.335 | 5063.34 | 0.1004 | 7.17583 | 58.4 |
| 29.0316 | 4396.74 | 0.0836 | 3.07579 | 50.71 |
| 27.0823 | 4235.59 | 0.0836 | 3.29258 | 48.85 |
| Peaks (All) | | | | |
| 6.7857 | 1705.57 | 0.0836 | 13.02663 | 19.67 |
| 10.8529 | 198.13 | 0.0836 | 8.1522 | 2.29 |
| 12.335 | 5063.34 | 0.1004 | 7.17583 | 58.4 |
| 14.4566 | 8669.85 | 0.0836 | 6.12715 | 100 |
| 16.3983 | 470.36 | 0.0669 | 5.40575 | 5.43 |
| 16.9757 | 538.35 | 0.1004 | 5.22316 | 6.21 |
| 17.416 | 257.63 | 0.0836 | 5.0921 | 2.97 |
| 19.7905 | 2007.61 | 0.0836 | 4.48617 | 23.16 |
| 20.2548 | 1434.71 | 0.1004 | 4.38438 | 16.55 |
| 20.6152 | 1169.49 | 0.0669 | 4.30852 | 13.49 |
| 21.0132 | 3793.73 | 0.1171 | 4.22782 | 43.76 |
| 21.7146 | 6282.16 | 0.1004 | 4.09281 | 72.46 |
| 22.7615 | 3239.73 | 0.1004 | 3.90688 | 37.37 |
| 23.0013 | 484.28 | 0.1004 | 3.86669 | 5.59 |
| 23.3254 | 431.06 | 0.1171 | 3.81369 | 4.97 |
| 24.7187 | 758.12 | 0.0669 | 3.60179 | 8.74 |
| 25.8948 | 817.29 | 0.1506 | 3.44081 | 9.43 |
| 27.0823 | 4235.59 | 0.0836 | 3.29258 | 48.85 |
| 28.6898 | 652.33 | 0.0836 | 3.11165 | 7.52 |
| 29.0316 | 4396.74 | 0.0836 | 3.07579 | 50.71 |
| 30.4594 | 133.22 | 0.0836 | 2.93479 | 1.54 |
| 31.2926 | 291.4 | 0.1004 | 2.85852 | 3.36 |
| 31.6493 | 267.88 | 0.0836 | 2.82711 | 3.09 |
| 32.3162 | 129.32 | 0.1004 | 2.77028 | 1.49 |

TABLE 2-continued

XRPD Peaks for (N,N-Diethylcarbamoyl)methyl
methyl (2E)but-2-ene-1,4-dioate: Form 1

| Pos. [°2Th.] | Height [cts] | FWHM [°2Th.] | d-spacing [Å] | Rel. Int. [%] |
|---|---|---|---|---|
| 32.7633 | 277.88 | 0.1171 | 2.73349 | 3.21 |
| 33.5857 | 76.32 | 0.1004 | 2.66841 | 0.88 |
| 34.026 | 399.82 | 0.0502 | 2.63488 | 4.61 |
| 35.3367 | 73.67 | 0.1338 | 2.5401 | 0.85 |
| 35.6451 | 86.4 | 0.1004 | 2.51882 | 1 |
| 37.1955 | 121.88 | 0.0502 | 2.41732 | 1.41 |
| 38.2248 | 40.9 | 0.2007 | 2.35456 | 0.47 |
| 39.0281 | 109.27 | 0.0836 | 2.30793 | 1.26 |

While the entire diffractogram of FIG. 1 can be used to characterize form 1, form 1 can also be accurately characterized with a subset of that data.

In certain embodiments, form 1 of (N,N-Diethylcarbamoyl)methyl methyl (2E)but-2-ene-1,4-dioate exhibits characteristic scattering angles (2θ) at least at 14.5±0.2°, 21.7±0.2°, 12.3±0.2°, 29.0±0.2°, and 27.1±0.2° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.2°, 21.7±0.2°, 12.3±0.2°, 29.0±0.2°, 27.1±0.2°, 21.0±0.2°, 22.8±0.2°, 19.8±0.2°, 6.8±0.2°, and 20.3±0.2° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.2°, 21.7±0.2°, 12.3±0.2°, 29.0±0.2°, 27.1±0.2°, 21.0±0.2°, 22.8±0.2°, 19.8±0.2°, 6.8±0.2°, 20.3±0.2°, 20.6±0.2°, 25.9±0.2°, 24.7±0.2°, 28.7±0.2° and 17.0±0.2° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.1°, 21.7±0.1°, 12.3±0.1°, 29.0±0.1°, and 27.1±0.1° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.1°, 21.7±0.1°, 12.3±0.1°, 29.0±0.1°, 27.1±0.1°, 21.0±0.1°, 22.8±0.1°, 19.8±0.1°, 6.8±0.1° and 20.3±0.1° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.1°, 21.7±0.1°, 12.3±0.1°, 29.0±0.1°, 27.1±0.1°, 21.0±0.1°, 22.8±0.1°, 19.8±0.1°, 6.8±0.1°, 20.3±0.1°, 20.6±0.1°, 25.9±0.1°, 24.7±0.1°, 28.7±0.1° and 17.0±0.1° in an X-ray powder diffraction pattern measured using Cu—K$_\alpha$ radiation.

Figure 2:
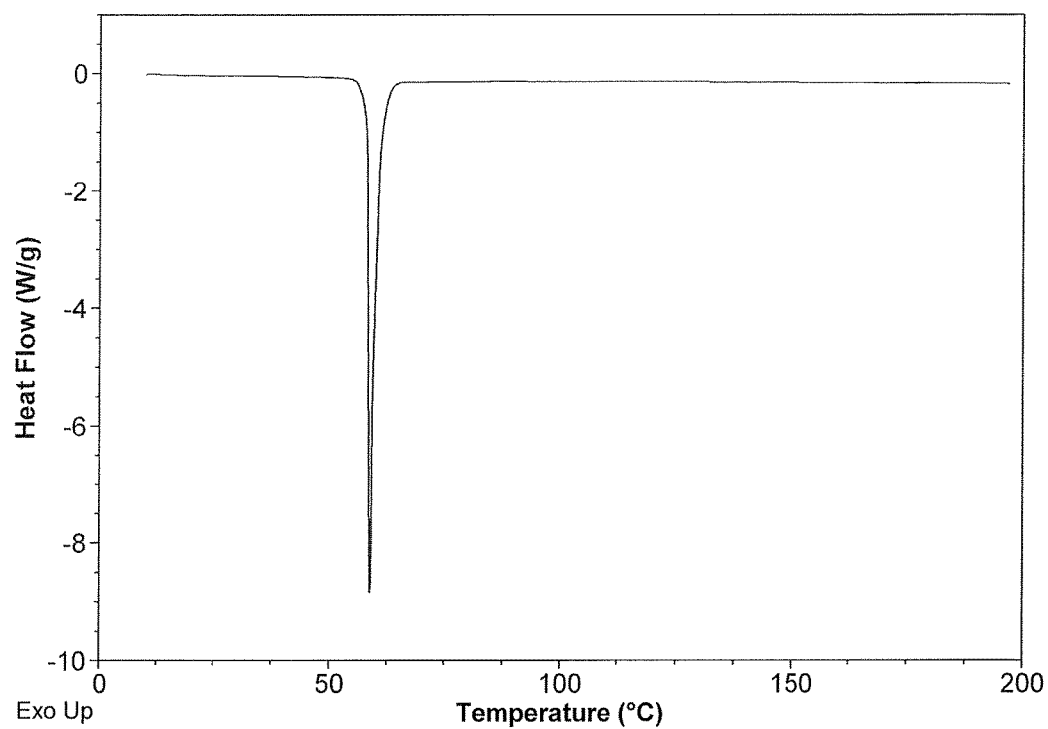
FIG. 2 is a differential scanning calorimetry (DSC) thermogram of a crystalline form 1 of (N,N-Diethylcarbamoyl)methyl methyl (2E)but-2-ene-1,4-dioate.

FIG. 2 is a differential scanning calorimetry (DSC) thermogram of form 1 of the (N,N-Diethylcarbamoyl)methyl methyl (2E)but-2-ene-1,4-dioate. The thermogram shows the form 1 has a melting point of about 58° C.

Figure 3:
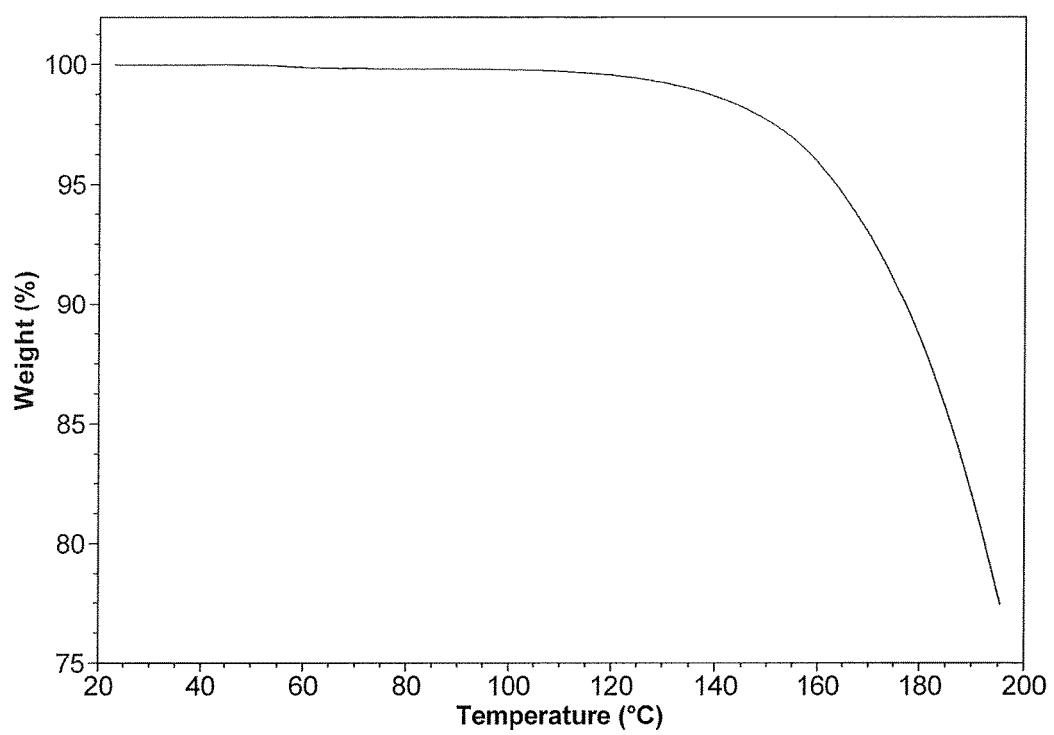
FIG. 3 is thermal gravimetric analysis (TGA) thermogram of a crystalline form 1 of (N,N-Diethylcarbamoyl)methyl methyl (2E)but-2-ene-1,4-dioate.

FIG. 3 is a thermal gravimetric analysis (TGA) thermogram of crystalline form 1 of (N,N-Diethylcarbamoyl)methyl methyl (2E)but-2-ene-1,4-dioate.

(N,N-Diethylcarbamoyl)methyl methyl (2E)but-2-ene-1,4-dioate: Form 2

One crystalline form disclosed herein is form 2 of (N,N-Diethylcarbamoyl)methyl methyl (2E)but-2-ene-1,4-dioate. Differential scanning calorimetry (DSC) analysis of this form 2 shows a melting point between about 48° C. and about 52° C., in certain embodiments between about 49° C. and about 51° C., and in certain embodiments at about 50° C.

The purity of crystalline form 2 of (N,N-Diethylcarbamoyl)methyl methyl (2E)but-2-ene-1,4-dioate is at least 99 wt % as measured by HPLC. In certain embodiments the purity of crystalline form 2 is at least 99.5 wt % as measured by HPLC. In certain embodiments the purity of crystalline form 2 is at least 99.9 wt % as measured by HPLC.

Figure 4:
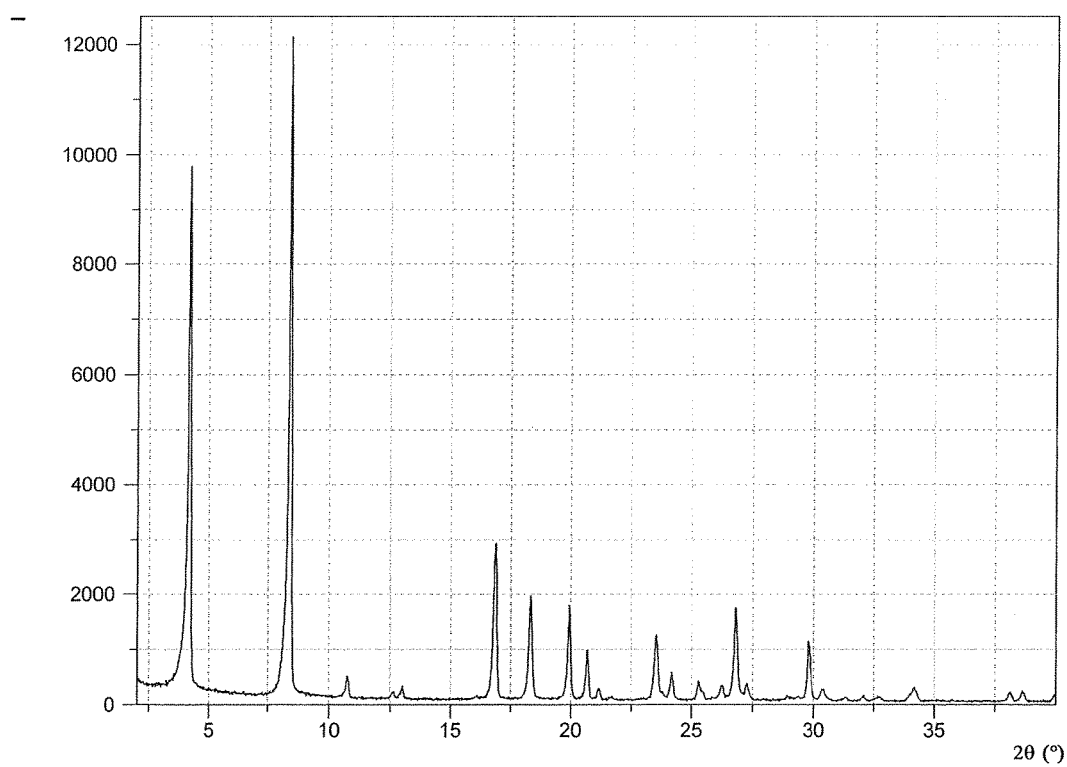
FIG. 4 is an X-ray powder diffractogram (XRPD) of a crystalline form 2 of (N,N-Diethylcarbamoyl)methyl methyl (2E)but-2-ene-1,4-dioate.

FIG. 4 is an X-ray powder diffractogram (XRPD) of form 2 of (N,N-Diethylcarbamoyl)methyl methyl (2E)but-2-ene-1,4-dioate showing the diffraction pattern measured using Cu—K$_\alpha$ radiation. Table 3 lists the approximate numerical values of the XRPD peak positions of the FIG. 4 diffractogram.

TABLE 3

XRPD Peaks for (N,N-Diethylcarbamoyl)methyl methyl
(2E)but-2-ene-1,4-dioate: Form 2

| Pos. [°2Th.] | Height [cts] | FWHM [°2Th.] | d-spacing [Å] | Rel. Int. [%] |
|---|---|---|---|---|
| Peaks (5 Highest Peaks) | | | | |
| 8.4278 | 11312.51 | 0.1171 | 10.49174 | 100 |
| 4.215 | 9229.54 | 0.1004 | 20.96408 | 81.59 |
| 16.8927 | 2677.65 | 0.184 | 5.24863 | 23.67 |
| 18.3421 | 1829.76 | 0.1338 | 4.83704 | 16.17 |
| 19.94 | 1677.6 | 0.1338 | 4.45287 | 14.83 |
| Peaks (All) | | | | |
| 4.215 | 9229.54 | 0.1004 | 20.96408 | 81.59 |
| 8.4278 | 11312.51 | 0.1171 | 10.49174 | 100 |
| 10.7747 | 375.29 | 0.1004 | 8.2112 | 3.32 |
| 12.6323 | 114.89 | 0.1004 | 7.00762 | 1.02 |
| 13.023 | 215.68 | 0.0669 | 6.79824 | 1.91 |
| 16.8927 | 2677.65 | 0.184 | 5.24863 | 23.67 |
| 18.3421 | 1829.76 | 0.1338 | 4.83704 | 16.17 |
| 19.94 | 1677.6 | 0.1338 | 4.45287 | 14.83 |
| 20.6716 | 906.31 | 0.1004 | 4.29691 | 8.01 |
| 21.1191 | 180.15 | 0.1171 | 4.20685 | 1.59 |
| 23.5364 | 1174.76 | 0.1673 | 3.77998 | 10.38 |
| 24.1612 | 475.39 | 0.0836 | 3.68363 | 4.2 |
| 25.2828 | 322.32 | 0.0836 | 3.5227 | 2.85 |
| 26.2305 | 257.88 | 0.1506 | 3.39754 | 2.28 |
| 26.8051 | 1668.51 | 0.1506 | 3.326 | 14.75 |
| 27.271 | 298.92 | 0.1004 | 3.27023 | 2.64 |
| 28.9259 | 81.8 | 0.1004 | 3.08679 | 0.72 |
| 29.7727 | 1023.91 | 0.102 | 2.99841 | 9.05 |
| 29.849 | 862.49 | 0.0612 | 2.99835 | 7.62 |
| 30.3802 | 197.39 | 0.204 | 2.93982 | 1.74 |
| 31.3336 | 54.91 | 0.1224 | 2.85251 | 0.49 |
| 32.0775 | 76.44 | 0.1224 | 2.78803 | 0.68 |
| 32.7483 | 60.19 | 0.3672 | 2.73244 | 0.53 |
| 34.1585 | 232.57 | 0.1224 | 2.62279 | 2.06 |
| 38.0932 | 161.38 | 0.1224 | 2.36044 | 1.43 |
| 38.6274 | 167.17 | 0.204 | 2.32901 | 1.48 |

While the entire diffractogram of FIG. 4 can be used to characterize form 2, form 2 can also be accurately characterized with a subset of that data.

In certain embodiments, form 2 of (N,N-Diethylcarbamoyl)methyl methyl (2E)but-2-ene-1,4-dioate exhibits characteristic scattering angles (2θ) at least at 8.4±0.2°, 4.2±0.2°, 16.9±0.2°, 18.3±0.2°, and 20.0±0.2° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.2°, 4.2±0.2°, 16.9±0.2°, 18.3±0.2°, 20.0±0.2°, 26.8±0.2°, 23.5±0.2°, 29.8±0.2°, 20.7±0.2°, and 24.2±0.2° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.2°, 4.2±0.2°, 16.9±0.2°, 18.3±0.2°, 20.0±0.2°, 26.8±0.2°, 23.5±0.2°, 29.8±0.2°, 20.7±0.2°, 24.2±0.2°, 10.8±0.2°, 25.3±0.2°, 27.3±0.2°, 26.2±0.2° and 34.2±0.2° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.1°, 4.2±0.1°, 16.9±0.1°, 18.3±0.1°, and 20.0±0.1° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.1°, 4.2±0.1°, 16.9±0.1°, 18.3±0.1°, 20.0±0.1°, 26.8±0.1°, 23.5±0.1°, 29.8±0.1°, 20.7±0.1° and 24.2±0.1° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.1°, 4.2±0.1°, 16.9±0.1°, 18.3±0.1°, 20.0±0.1°, 26.8±0.1°, 23.5±0.1°, 29.8±0.1°, 20.7±0.1°, 24.2±0.1°, 10.8±0.1°, 25.3±0.1°, 27.3±0.1°, 26.2±0.1° and 34.2±0.1° in an X-ray powder diffraction pattern measured using Cu—K$_\alpha$ radiation.

Figure 5:
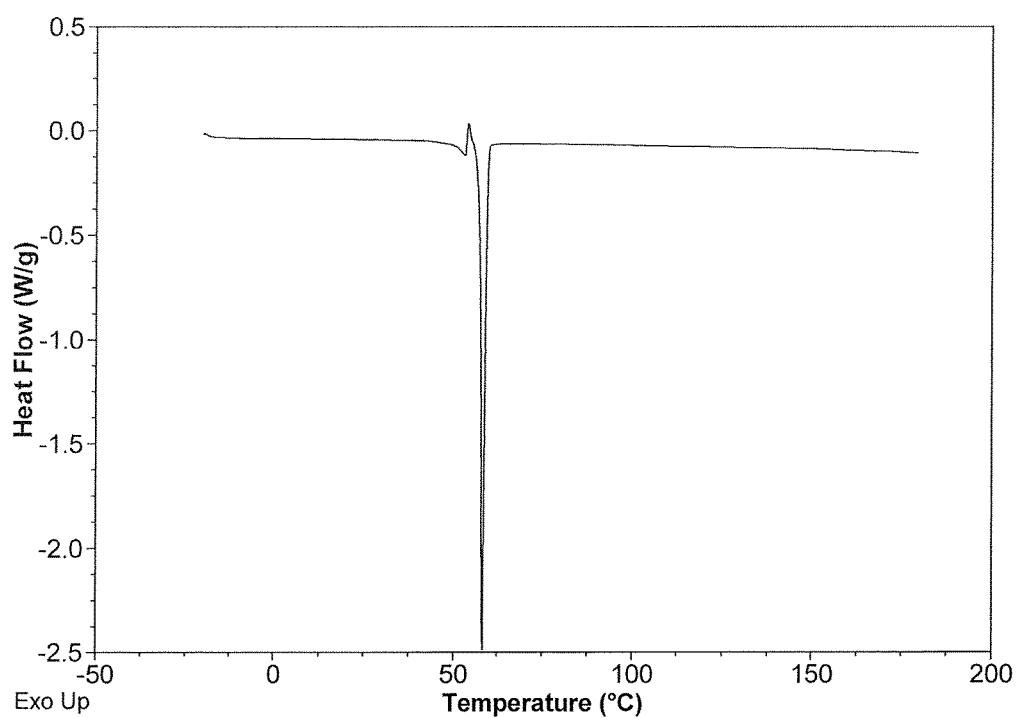
FIG. 5 is a differential scanning calorimetry (DSC) thermogram of a crystalline form 2 of (N,N-Diethylcarbamoyl)methyl methyl (2E)but-2-ene-1,4-dioate.

FIG. 5 is a differential scanning calorimetry (DSC) thermogram of form 2 of the (N,N-Diethylcarbamoyl)methyl methyl (2E)but-2-ene-1,4-dioate. The thermogram shows form 2 has a melting point of about 50° C.

Figure 6:
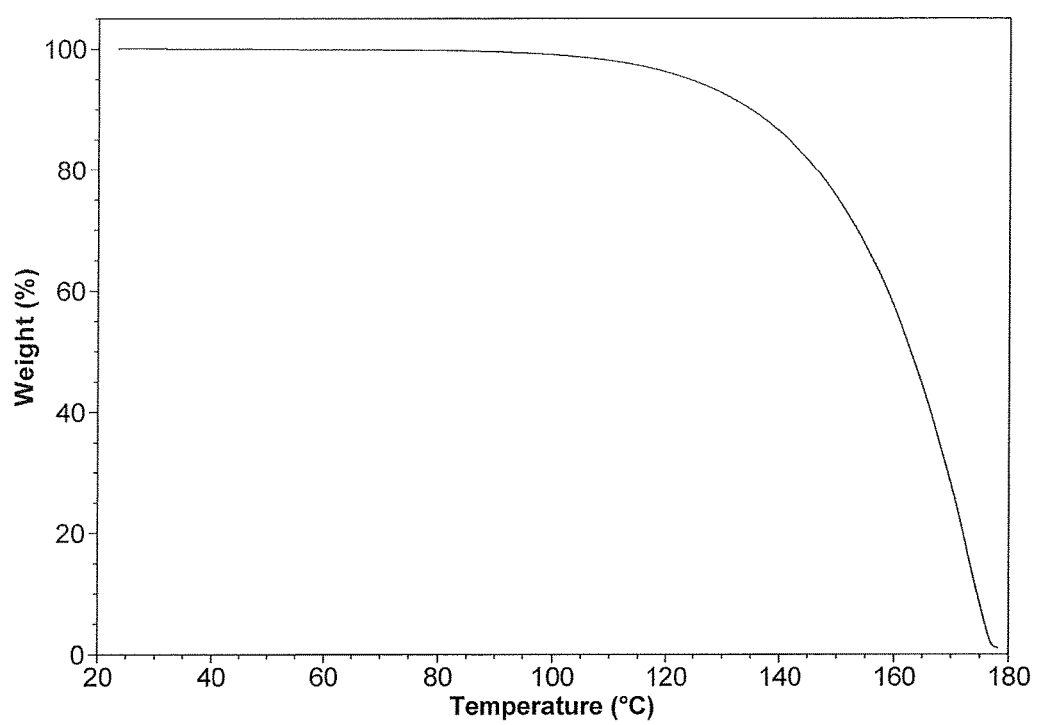
FIG. 6 is thermal gravimetric analysis (TGA) thermogram of a crystalline form 2 of (N,N-Diethylcarbamoyl)methyl methyl (2E)but-2-ene-1,4-dioate.

FIG. 6 is a thermal gravimetric analysis (TGA) thermogram of crystalline form 2 of (N,N-Diethylcarbamoyl)methyl methyl (2E)but-2-ene-1,4-dioate.

(N,N-Diethylcarbamoyl)methyl methyl (2E)but-2-ene-1,4-dioate: Form 3

One crystalline form disclosed herein is form 3 of (N,N-Diethylcarbamoyl)methyl methyl (2E)but-2-ene-1,4-dioate. Differential scanning calorimetry (DSC) analysis of this form 3 shows a melting point between about 45° C. and about 49° C., in certain embodiments between about 46° C. and about 48° C., and in certain embodiments at about 47° C.

The purity of crystalline form 3 of (N,N-Diethylcarbamoyl)methyl methyl (2E)but-2-ene-1,4-dioate is at least 99 wt % as measured by HPLC. In certain embodiments the purity of crystalline form 3 is at least 99.5 wt % as measured by HPLC. In certain embodiments the purity of crystalline form 3 is at least 99.9 wt % as measured by HPLC.

Figure 7:
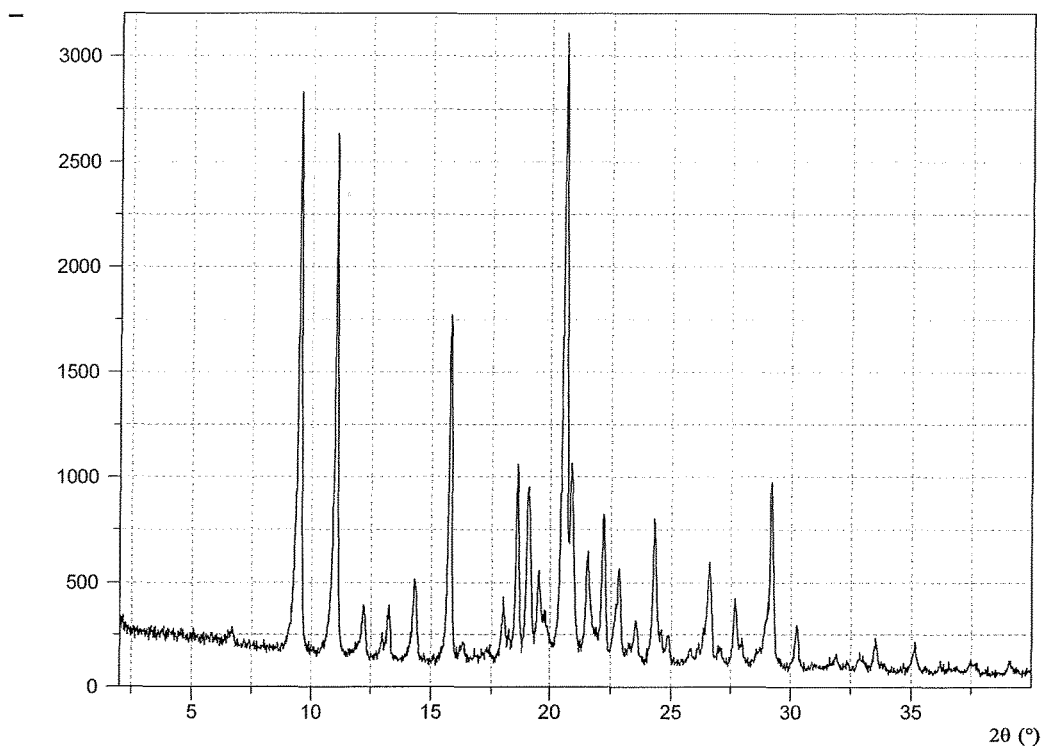
FIG. 7 is an X-ray powder diffractogram (XRPD) of a crystalline form 3 of (N,N-Diethylcarbamoyl)methyl methyl (2E)but-2-ene-1,4-dioate.

FIG. 7 is an X-ray powder diffractogram (XRPD) of form 3 of (N,N-Diethylcarbamoyl)methyl methyl (2E)but-2-ene-1,4-dioate showing the diffraction pattern measured using Cu—K$_\alpha$ radiation. Table 4 lists the approximate numerical values of the XRPD peak positions of the FIG. 7 diffractogram.

TABLE 4

XRPD Peaks for (N,N-Diethylcarbamoyl)methyl methyl (2E)but-2-ene-1,4-dioate: Form 3

| Pos. [°2Th.] | Height [cts] | FWHM [°2Th.] | d-spacing [Å] | Rel. Int. [%] |
|---|---|---|---|---|
| Peaks (5 Highest Peaks) | | | | |
| 20.6122 | 2941.88 | 0.1338 | 4.30916 | 100 |
| 9.5381 | 2619.16 | 0.1004 | 9.27285 | 89.03 |
| 11.0718 | 2440.32 | 0.1004 | 7.99154 | 82.95 |
| 15.8074 | 1610.75 | 0.1004 | 5.60648 | 54.75 |
| 18.5914 | 933.36 | 0.1338 | 4.77272 | 31.73 |
| Peaks (All) | | | | |
| 9.5381 | 2619.16 | 0.1004 | 9.27285 | 89.03 |
| 11.0718 | 2440.32 | 0.1004 | 7.99154 | 82.95 |
| 12.2024 | 217.18 | 0.1338 | 7.25351 | 7.38 |
| 13.2605 | 219.31 | 0.1171 | 6.677 | 7.45 |
| 14.3131 | 381.18 | 0.1506 | 6.18824 | 12.96 |
| 15.8074 | 1610.75 | 0.1004 | 5.60648 | 54.75 |
| 16.3081 | 78.28 | 0.2007 | 5.43546 | 2.66 |
| 18.0005 | 290 | 0.1673 | 4.92804 | 9.86 |
| 18.5914 | 933.36 | 0.1338 | 4.77272 | 31.73 |
| 19.059 | 829.03 | 0.0836 | 4.65666 | 28.18 |
| 19.5156 | 398.86 | 0.1171 | 4.54874 | 13.56 |
| 20.6122 | 2941.88 | 0.1338 | 4.30916 | 100 |
| 20.849 | 911.14 | 0.1171 | 4.26073 | 30.97 |
| 21.5204 | 505.59 | 0.1171 | 4.12931 | 17.19 |
| 22.191 | 706.92 | 0.1171 | 4.00602 | 24.03 |
| 22.8235 | 454.03 | 0.1171 | 3.89642 | 15.43 |
| 23.5381 | 206.41 | 0.1506 | 3.77971 | 7.02 |
| 24.3024 | 685.9 | 0.1338 | 3.66254 | 23.31 |
| 24.8546 | 140.84 | 0.1338 | 3.58241 | 4.79 |
| 26.6025 | 506.3 | 0.1506 | 3.35087 | 17.21 |
| 27.6745 | 302.27 | 0.1338 | 3.22345 | 10.27 |
| 29.1631 | 876.91 | 0.1338 | 3.06222 | 29.81 |
| 30.2144 | 205.43 | 0.1171 | 2.95802 | 6.98 |
| 31.8002 | 44.76 | 0.4015 | 2.81404 | 1.52 |
| 32.9135 | 54.11 | 0.2676 | 2.72136 | 1.84 |
| 33.5305 | 133.79 | 0.1338 | 2.67268 | 4.55 |
| 35.1623 | 123.35 | 0.1338 | 2.5523 | 4.19 |
| 37.5326 | 48.52 | 0.3346 | 2.39638 | 1.65 |
| 39.1007 | 49.52 | 0.2007 | 2.30381 | 1.68 |

While the entire diffractogram of FIG. 7 can be used to characterize form 3, form 3 can also be accurately characterized with a subset of that data.

In certain embodiments, form 3 of (N,N-Diethylcarbamoyl)methyl methyl (2E)but-2-ene-1,4-dioate exhibits characteristic scattering angles (2θ) at least at 20.6±0.2°, 9.5±0.2°, 11.1±0.2°, 15.8±0.2°, and 18.6±0.2° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.2°, 9.5±0.2°, 11.1±0.2°, 15.8±0.2°, 18.6±0.2°, 20.8±0.2°, 29.2±0.2°, 19.1±0.2°, 22.2±0.2°, and 24.3±0.2° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.2°, 9.5±0.2°, 11.1±0.2°, 15.8±0.2°, 18.6±0.2°, 20.8±0.2°, 29.2±0.2°, 19.1±0.2°, 22.2±0.2°, 24.3±0.2°, 26.6±0.2°, 21.5±0.2°, 22.8±0.2°, 19.5±0.2° and 14.3±0.2° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.1°, 9.5±0.1°, 11.1±0.1°, 15.8±0.1°, and 18.6±0.1° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.1°, 9.5±0.1°, 11.1±0.1°, 15.8±0.1°, 18.6±0.1°, 20.8±0.1°, 29.2±0.1°, 19.1±0.1°, 22.2±0.1°, and 24.3±0.1° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.1°, 9.5±0.1°, 11.1±0.1°, 15.8±0.1°, 18.6±0.1°, 20.8±0.1°, 29.2±0.1°, 19.1±0.1°, 22.2±0.1°, 24.3±0.1°, 26.6±0.1°, 21.5±0.1°, 22.8±0.1°, 19.5±0.1° and 14.3±0.1° in an X-ray powder diffraction pattern measured using Cu—K$_\alpha$ radiation.

Figure 8:
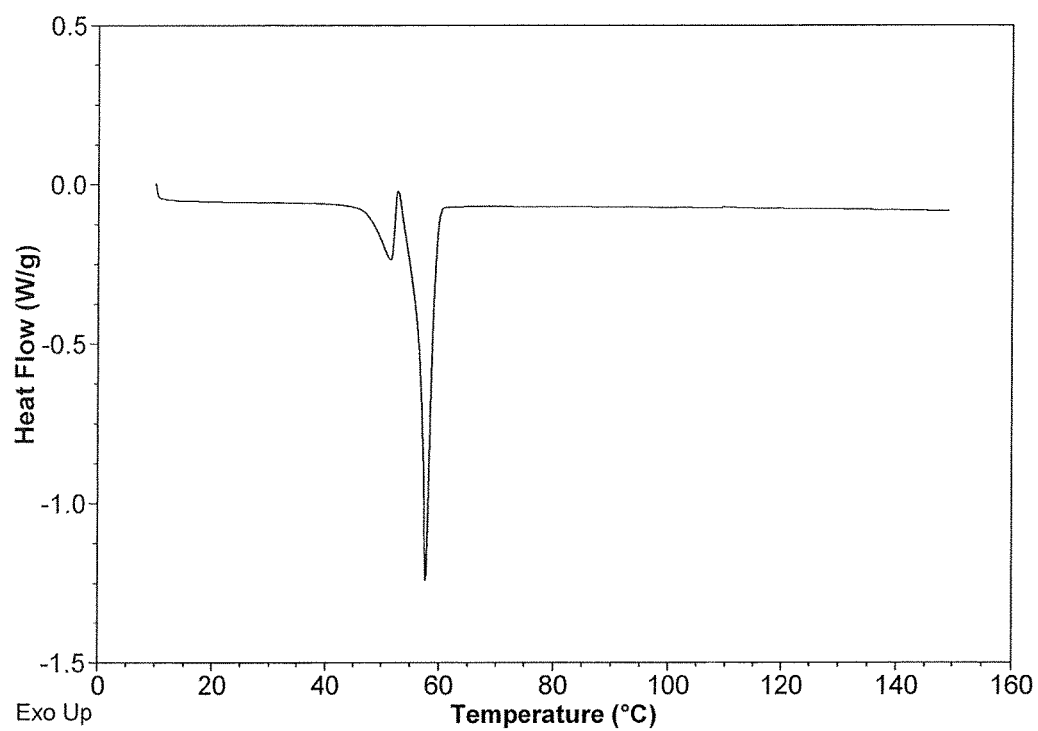
FIG. 8 is a differential scanning calorimetry (DSC) thermogram of a crystalline form 3 of (N,N-Diethylcarbamoyl)methyl methyl (2E)but-2-ene-1,4-dioate.

FIG. 8 is a differential scanning calorimetry (DSC) thermogram of form 3 of the (N,N-Diethylcarbamoyl)methyl methyl (2E)but-2-ene-1,4-dioate. The thermogram shows the form 3 has a melting point of about 47° C.

Figure 9:
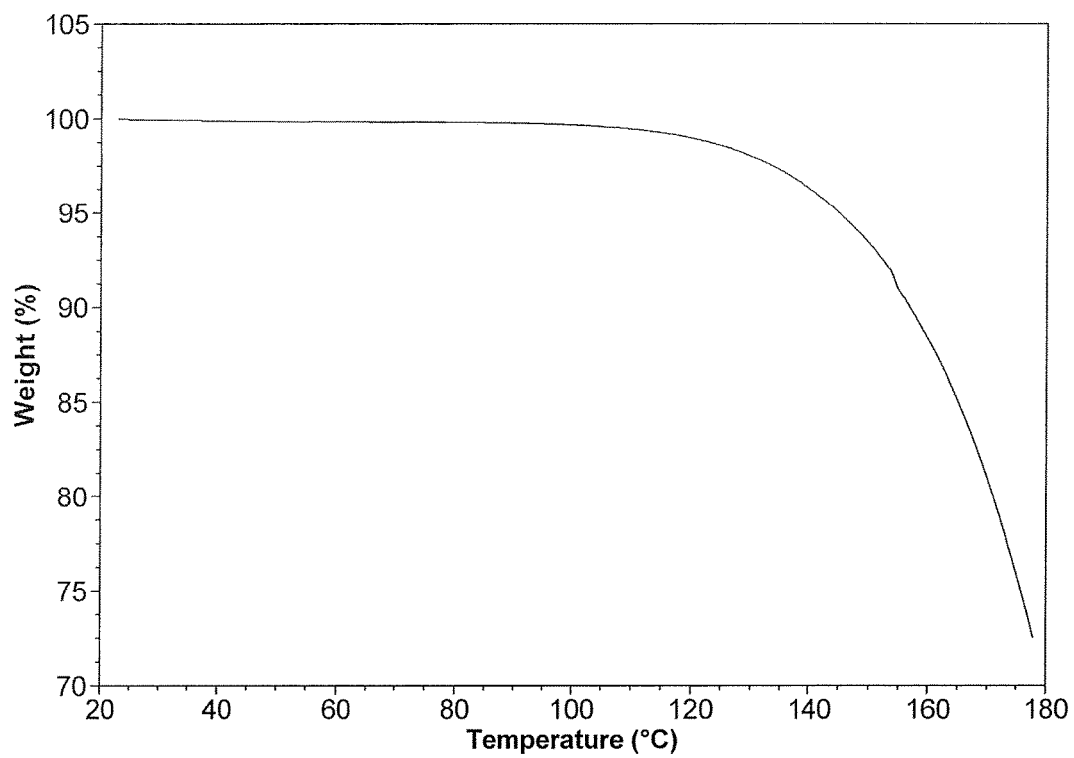
FIG. 9 is thermal gravimetric analysis (TGA) thermogram of a crystalline form 3 of (N,N-Diethylcarbamoyl)methyl methyl (2E)but-2-ene-1,4-dioate.

FIG. 9 is a thermal gravimetric analysis (TGA) thermogram of crystalline form 3 of (N,N-Diethylcarbamoyl)methyl methyl (2E)but-2-ene-1,4-dioate.

(N,N-Diethylcarbamoyl)methyl methyl (2E)but-2-ene-1,4-dioate: Form 4

One crystalline form disclosed herein is form 4 of (N,N-Diethylcarbamoyl)methyl methyl (2E)but-2-ene-1,4-dioate. Differential scanning calorimetry (DSC) analysis of this form 4 shows a polymorphic transformation between about 36° C. and about 40° C., in certain embodiments between about 37° C. and about 39° C., and in certain embodiments at about 38° C.

The purity of crystalline form 4 of (N,N-Diethylcarbamoyl)methyl methyl (2E)but-2-ene-1,4-dioate is at least 99 wt % as measured by HPLC. In certain embodiments the purity of crystalline form 4 is at least 99.5 wt % as measured by HPLC. In certain embodiments the purity of crystalline form 4 is at least 99.9 wt % as measured by HPLC.

Figure 10:
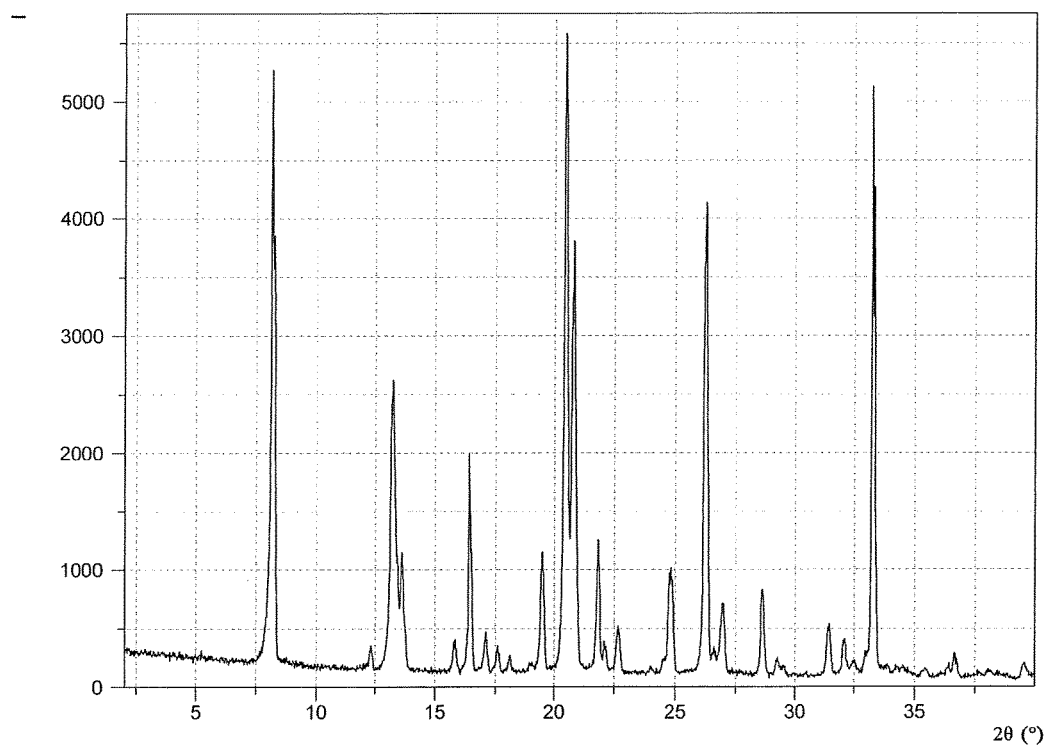
FIG. 10 is an X-ray powder diffractogram (XRPD) of a crystalline form 4 of (N,N-Diethylcarbamoyl)methyl methyl (2E)but-2-ene-1,4-dioate.

FIG. 10 is an X-ray powder diffractogram (XRPD) of form 4 of the (N,N-Diethylcarbamoyl)methyl methyl (2E)but-2-ene-1,4-dioate showing the diffraction pattern measured using Cu—K$_\alpha$ radiation. Table 5 lists the approximate numerical values of the XRPD peak positions of the FIG. 10 diffractogram.

TABLE 5

XRPD Peaks for (N,N-Diethylcarbamoyl)methyl methyl (2E)but-2-ene-1,4-dioate: Form 4

| Pos. [°2Th.] | Height [cts] | FWHM [°2Th.] | d-spacing [Å] | Rel. Int. [%] |
|---|---|---|---|---|
| Peaks (5 Highest Peaks) | | | | |
| 20.4421 | 5428.16 | 0.1338 | 4.34461 | 100 |
| 8.1616 | 5069.85 | 0.0669 | 10.8333 | 93.4 |
| 33.2225 | 4743.54 | 0.0502 | 2.69675 | 87.39 |
| 26.2929 | 4071.97 | 0.0669 | 3.38962 | 75.02 |
| 20.8019 | 3710.75 | 0.0836 | 4.27029 | 68.36 |
| Peaks (All) | | | | |
| 8.1616 | 5069.85 | 0.0669 | 10.8333 | 93.4 |
| 8.2731 | 3453.55 | 0.0502 | 10.68762 | 63.62 |
| 12.3278 | 178.49 | 0.1338 | 7.17997 | 3.29 |
| 13.1556 | 2023.81 | 0.1673 | 6.73003 | 37.28 |
| 13.6427 | 964.42 | 0.0836 | 6.49081 | 17.77 |
| 15.8255 | 262.36 | 0.1506 | 5.6001 | 4.83 |
| 16.4155 | 1677.54 | 0.0502 | 5.40014 | 30.9 |

TABLE 5-continued

XRPD Peaks for (N,N-Diethylcarbamoyl)methyl methyl (2E)but-2-ene-1,4-dioate: Form 4

| Pos. [°2Th.] | Height [cts] | FWHM [°2Th.] | d-spacing [Å] | Rel. Int. [%] |
|---|---|---|---|---|
| 17.1332 | 312.18 | 0.1673 | 5.17549 | 5.75 |
| 17.6134 | 182.86 | 0.1338 | 5.03547 | 3.37 |
| 18.1058 | 119.69 | 0.1004 | 4.89963 | 2.21 |
| 19.4519 | 904.34 | 0.184 | 4.56349 | 16.66 |
| 20.4421 | 5428.16 | 0.1338 | 4.34461 | 100 |
| 20.8019 | 3710.75 | 0.0836 | 4.27029 | 68.36 |
| 21.8182 | 1151.17 | 0.1338 | 4.07361 | 21.21 |
| 22.1297 | 223.05 | 0.1338 | 4.01696 | 4.11 |
| 22.6845 | 376.22 | 0.1506 | 3.91997 | 6.93 |
| 24.7372 | 700.3 | 0.1004 | 3.59914 | 12.9 |
| 26.2091 | 3212.01 | 0.0816 | 3.39745 | 59.17 |
| 26.2929 | 4071.97 | 0.0669 | 3.38962 | 75.02 |
| 26.9684 | 604.96 | 0.184 | 3.30623 | 11.14 |
| 28.6594 | 687.82 | 0.1506 | 3.11488 | 12.67 |
| 29.2511 | 132.28 | 0.1338 | 3.05321 | 2.44 |
| 31.4215 | 403.53 | 0.2007 | 2.84708 | 7.43 |
| 32.0747 | 298.8 | 0.1673 | 2.79058 | 5.5 |
| 33.2225 | 4743.54 | 0.0502 | 2.69675 | 87.39 |
| 35.4358 | 60.12 | 0.2007 | 2.53322 | 1.11 |
| 36.6746 | 177.18 | 0.1673 | 2.45045 | 3.26 |
| 39.5373 | 106.51 | 0.1673 | 2.27938 | 1.96 |

While the entire diffractogram of FIG. 10 can be used to characterize form 4, form 4 can also be accurately characterized with a subset of that data.

In certain embodiments, form 4 of (N,N-Diethylcarbamoyl)methyl methyl (2E)but-2-ene-1,4-dioate exhibits characteristic scattering angles (2θ) at least at 20.4±0.2°, 8.2±0.2°, 33.2±0.2°, 26.3±0.2°, and 20.8±0.2° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.2°, 8.2±0.2°, 33.2±0.2°, 26.3±0.2°, 20.8±0.2°, 8.3±0.2°, 26.2±0.2°, 13.2±0.2°, 16.4±0.2°, and 21.8±0.2° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.2°, 8.2±0.2°, 33.2±0.2°, 26.3±0.2°, 20.8±0.2°, 8.3±0.2°, 26.2±0.2°, 13.2±0.2°, 16.4±0.2°, 21.8±0.2°, 13.6±0.2°, 19.4±0.2°, 24.7±0.2°, 28.7±0.2°, and 27.0±0.2° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.1°, 8.2±0.1°, 33.2±0.1°, 26.3±0.1°, and 20.8±0.1° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.1°, 8.2±0.1°, 33.2±0.1°, 26.3±0.1°, 20.8±0.1°, 8.3±0.1°, 26.2±0.1°, 13.2±0.1°, 16.4±0.1°, and 21.8±0.1° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.1°, 8.2±0.1°, 33.2±0.1°, 26.3±0.1°, 20.8±0.1°, 8.3±0.1°, 26.2±0.1°, 13.2±0.1°, 16.4±0.1°, 21.8±0.1°, 13.6±0.1°, 19.4±0.1°, 24.7±0.1°, 28.7±0.1°, and 27.0±0.1° in an X-ray powder diffraction pattern measured using Cu—K$_\alpha$ radiation.

Figure 11:
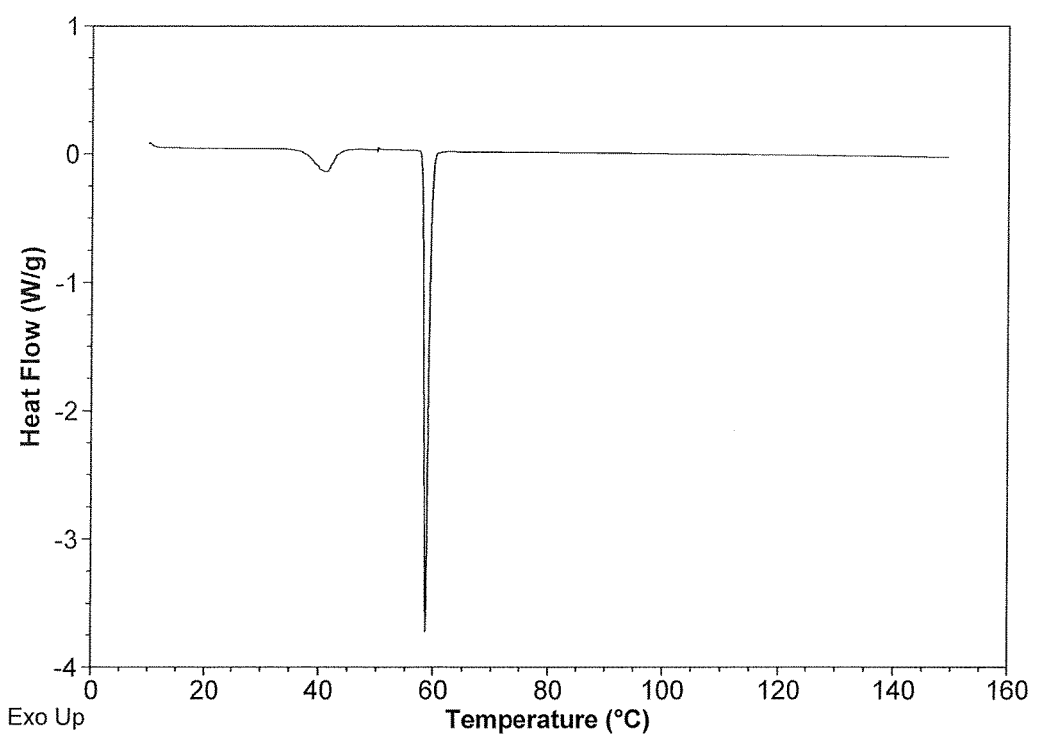
FIG. 11 is a differential scanning calorimetry (DSC) thermogram of a crystalline form 4 of (N,N-Diethylcarbamoyl)methyl methyl (2E)but-2-ene-1,4-dioate.

FIG. 11 is a differential scanning calorimetry (DSC) thermogram of form 4 of the (N,N-Diethylcarbamoyl) methyl methyl (2E)but-2-ene-1,4-dioate. The thermogram shows the form 4 has a melting point of about 38° C.

Figure 12:
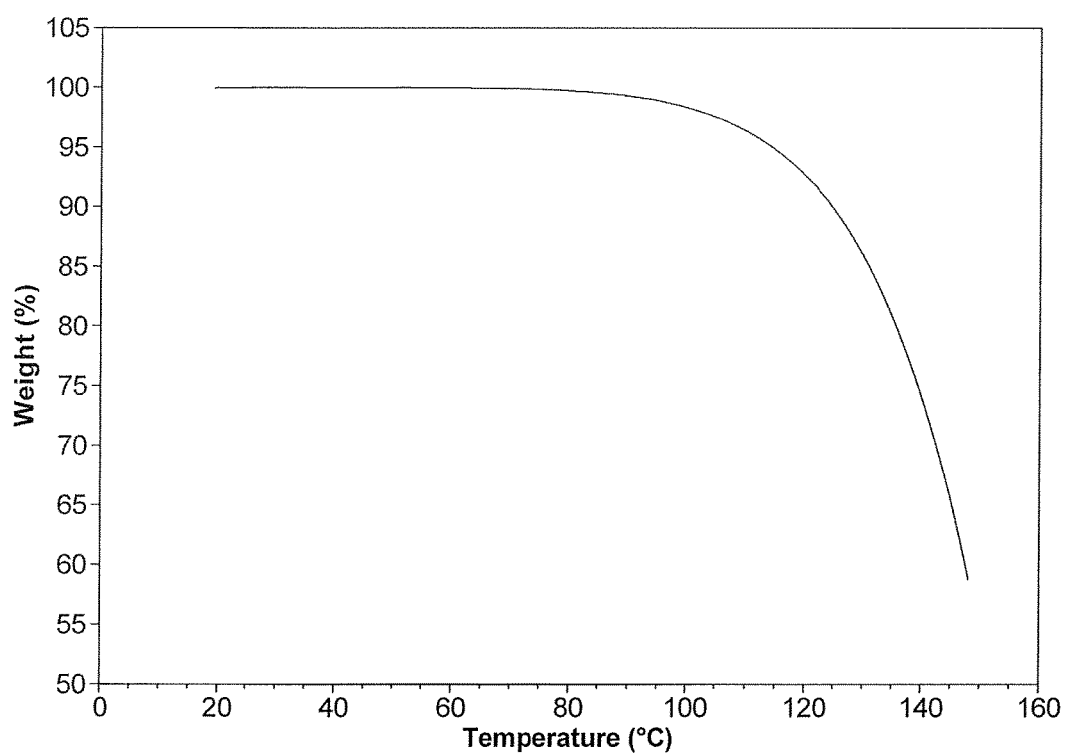
FIG. 12 is thermal gravimetric analysis (TGA) thermogram of a crystalline form 4 of (N,N-Diethylcarbamoyl)methyl methyl (2E)but-2-ene-1,4-dioate.

FIG. 12 is a thermal gravimetric analysis (TGA) thermogram of crystalline form 4 of (N,N-Diethylcarbamoyl) methyl methyl (2E)but-2-ene-1,4-dioate.

Pharmaceutical Compositions

The present disclosure relates to pharmaceutical compositions comprising a therapeutically effective amount of a crystalline form of (N,N-Diethylcarbamoyl)methyl methyl (2E)but-2-ene-1,4-dioate together with a suitable amount of one or more pharmaceutically acceptable vehicle so as to provide a composition for proper administration to a patient. The crystalline form 1, form 2, form 3, and form 4 of (N,N-Diethylcarbamoyl)methyl methyl (2E)but-2-ene-1,4-dioate disclosed herein have the same pharmaceutical activity as the respective active pharmaceutical ingredient (API). Suitable pharmaceutical vehicles are described in the art.

Pharmaceutical compositions for the treatment of any one or more diseases and disorders comprise a therapeutically effective amount of a crystalline form disclosed herein as appropriate for treatment of a patient with the particular disease(s) or disorder(s).

A pharmaceutical composition may be any pharmaceutical form which maintains the crystalline form of a disclosed crystalline form. In certain embodiments, the pharmaceutical composition may be selected from a solid form, a liquid suspension, an injectable composition, a topical form, and a transdermal form.

Depending on the type of pharmaceutical composition, the pharmaceutically acceptable vehicle may be chosen from any one or a combination of vehicles known in the art. The choice of the pharmaceutically acceptable vehicle depends upon the pharmaceutical form and the desired method of administration to be used. For a pharmaceutical composition comprising a crystalline form disclosed herein, a vehicle should be chosen that maintains the crystalline form. In other words, the vehicle should not substantially alter the crystalline form of the crystalline form. For example, a liquid vehicle which would dissolve the crystalline form should not be used. Nor should the vehicle be otherwise incompatible with a crystalline form, such as by producing any undesirable biological effect or otherwise interacting in a deleterious manner with any other component(s) of the pharmaceutical composition.

In some embodiments, the pharmaceutical compositions are formulated in unit dosage forms for ease of administration and uniformity of dosage. A "unit dosage form" refers to a physically discrete unit of therapeutic agent appropriate for the patient to be treated. It will be understood, however, that the total daily dosage of a crystalline form and its pharmaceutical compositions will typically be decided by the attending physician within the scope of sound medical judgment.

Because the crystalline forms disclosed herein are more easily maintained during their preparation, solid dosage forms may be employed in numerous embodiments for the pharmaceutical compositions. In some embodiments, solid dosage forms for oral administration include capsules, tablets, pills, powders, and granules. In such solid dosage forms, the active compound is mixed with at least one inert, pharmaceutically acceptable vehicle such as sodium citrate or dicalcium phosphate. The solid dosage form may also include one or more of: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) dissolution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate. The solid dosage forms may also comprise buffering agents. They may optionally comprise opacifying agents and can also be of a composition such that they release the active ingredient(s) only in a certain part of the intestinal tract, optionally, in a delayed manner. Remington's Pharmaceutical Sciences, Sixteenth Edition, E. W. Martin (Mack Publishing Co., Easton, Pa., 1980) discloses various vehicles used in formulating pharmaceutical compositions and known techniques for the preparation thereof. Solid dosage forms of pharmaceutical compositions can also be prepared with coatings and shells such as enteric coatings and other coatings well known in the pharmaceutical formulating art.

A crystalline form disclosed herein can be in a solid micro-encapsulated form with one or more vehicles as discussed above. Microencapsulated forms of a crystalline form may also be used in soft and hard-filled gelatin capsules with vehicles such as lactose or milk sugar as well as high molecular weight polyethylene glycols and the like.

Also disclosed herein are methods for the treatment of the disorders disclosed herein. The crystalline forms, and pharmaceutical compositions comprising them, may be administered using any amount, any form of pharmaceutical composition and any route of administration effective for the treatment. After formulation with an appropriate pharmaceutically acceptable vehicle in a desired dosage, as known by those of skill in the art, the pharmaceutical compositions can be administered to humans and other animals orally, rectally, parenterally, intravenously, intracisternally, intravaginally, intraperitoneally, topically (as by powders, ointments, or drops), bucally, as an oral or nasal spray, or the like, depending on the location and severity of the condition being treated. In certain embodiments, the crystalline forms may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject.

Therapeutic Uses

The crystalline forms 1, 2, 3, and 4 of (N,N-Diethylcarbamoyl)methyl methyl (2E)but-2-ene-1,4-dioate disclosed herein may be used to treat diseases, disorders, conditions, and/or symptoms of any disease or disorder for which MHF is known to provide, or is later found to provide, therapeutic benefit. MHF is known to be effective in treating psoriasis, multiple sclerosis, an inflammatory bowel disease, asthma, chronic obstructive pulmonary disease, and arthritis, among others. Hence, the crystalline forms 1, 2, 3, and 4 disclosed herein may be used to treat any one or more of the foregoing diseases and disorders. The underlying etiology of any of the foregoing diseases being treated may have a multiplicity of origins. Further, in certain embodiments, a therapeutically effective amount of one or more of the crystalline forms of (N,N-Diethylcarbamoyl)methyl methyl (2E)but-2-ene-1,4-dioate may be administered to a patient, such as a human, as a preventative measure against various diseases or disorders.

The crystalline forms 1, 2, 3, and 4 of (N,N-Diethylcarbamoyl)methyl methyl (2E)but-2-ene-1,4-dioate disclosed herein can be administered to a patient to treat or prevent any one or more of the diseases and conditions selected from: acute dermatitis, acute disseminated encephalomyelitis, Addison's disease, adrenal leukodystrophy, AGE-induced genome damage, Alexanders Disease, alopecia areata (totalis and universalis), Alper's Disease, Alzheimer's disease, amyotrophic lateral sclerosis, angina pectoris, ankylosing spondylitis, antiphospholipid antibody syndrome, arthritis, asthma, autoimmune carditis, autoimmune hemolytic anemia, autoimmune hepatitis, autoimmune inner ear disease, balo concentric sclerosis, Behcet's disease, bullous pemphigoid, Canavan disease, cardiac insufficiency including left ventricular insufficiency, celiac disease, central nervous system vasculitis, Chagas disease, Charcott-Marie-Tooth Disease, childhood ataxia with central nervous system hypomyelination, chronic dermatitis, chronic idiopathic peripheral neuropathy, chronic obstructive pulmonary disease, contact dermatitis, Crohn's disease, cutaneous Crohn's disease, cutaneous lupus, cutaneous sarcoidosis, dermatomyositis, diabetes mellitus type I, diabetic retinopathy, eczema, endometriosis, globoid cell leukodystrophy (Krabbe Disease), Goodpasture's syndrome, graft versus host disease, granulomas including annulaire, Graves' disease, Guillain-Barre syndrome, Hashimoto's disease, hepatitis C viral infection, herpes simplex viral infection, hidradenitis suppurativea, human immunodeficiency viral infection, Huntington's disease, idiopathic thrombocytopenic purpura, IgA neuropathy, inflammatory bowel disease, interstitial cystitis, irritable bowel disorder, ischemia, Kawasaki disease, lichen planus, lupus, lupus erythematosus, macular degeneration, mitochondrial encephalomyopathy, mixed connective tissue disease, monomelic amyotrophy, morphea, multiple sclerosis, myasthenia gravis, myocardial infarction, narcolepsy, neurodegeneration with brain iron accumulation, neuromyelitis optica, neuromyotonia, neurosarcoidosis, NF-κB mediated diseases, optic neuritis, pareneoplastic syndromes, Parkinson's disease, Pelizaeus-Merzbacher disease, pemphigus, pernicious anaemia, polymyositis, primary biliary cirrhosis, primary lateral sclerosis, progressive supranuclear palsy, psoriasis, psoriatic arthritis, pyoderma gangrenosum, reperfusion injury, retinopathia pigmentosa, rheumatica, sarcoidosis, Schilders Disease, schizophrena, scleroderma, Sjogren's syndrome, stiff person syndrome, subacute necrotizing myelopathy, susac syndrome, temporal arteritis, transplantation rejection, transverse myelitis, a tumor, ulcerative colitis, vasculitis, vitiligo, Wegener's granulomatosis and Zellweger's syndrome.

Efficacy of the crystalline forms 1, 2, 3 and 4 of (N,N-Diethylcarbamoyl)methyl methyl (2E)but-2-ene-1,4-dioate for treating any of the diseases and conditions listed can be determined using animal models and in clinical trials.

Psoriasis

Psoriasis is characterized by hyperkeratosis and thickening of the epidermis as well as by increased vascularity and infiltration of inflammatory cells in the dermis. Psoriasis vulgaris manifests as silvery, scaly, erythematous plaques on typically the scalp, elbows, knees, and buttocks. Guttate psoriasis occurs as tear-drop size lesions. Fumaric acid esters are recognized for the treatment of psoriasis and dimethyl fumarate is approved for the systemic treatment of psoriasis in Germany (Mrowietz and Asadullah, *Trends Mol Med* (2005), 11(1): 43-48; and Mrowietz et al., *Br J Dermatology* (1999), 141: 424-429).

Efficacy of the crystalline forms 1, 2, 3 and 4 of (N,N-Diethylcarbamoyl)methyl methyl (2E)but-2-ene-1,4-dioate for treating psoriasis can be determined using animal models and in clinical trials.

Multiple Sclerosis

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied, with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, *Lab Invest* (2001), 81: 263-281; and Virley, *NeuroRx* (2005), 2(4): 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances, spasticity, tremor, a lack of coordination, and visual impairment, any one of which negatively impacts the quality of life of the individual. The clinical course of MS can vary from individual to individual, but invariably the disease can be categorized in three forms: relapsing-remitting, secondary progressive, and primary progressive.

Studies support the efficacy of fumaric acid esters for treating MS and fumaric acid esters are presently undergoing phase II clinical testing for such treatment (Schimrigk et al., *Eur J Neurology* (2006), 13: 604-610; and Wakkee and Thio, *Current Opinion Investigational Drugs* (2007), 8(11): 955-962).

Assessment of MS treatment efficacy in clinical trials can be accomplished using tools such as the Expanded Disability Status Scale and the MS Functional, as well as magnetic resonance imaging, lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

The efficacy of the crystalline forms 1, 2, 3, and 4 of (N,N-Diethylcarbamoyl)methyl methyl (2E)but-2-ene-1,4-dioate for treating MS can be determined using animal models and in clinical trials.

EXAMPLES

Example 1

Synthesis, Purification and Analysis of Crystalline Form 1 of (N,N-Diethylcarbamoyl)methyl methyl (2E)but-2-ene-1,4-dioate Crystalline form 1 is the thermodynamically stable form at ambient temperature. Because of that, it can be produced by suspending an excess amount of (N,N-Diethylcarbamoyl)methyl methyl (2E)but-2-ene-1,4-dioate solid in an organic solvent for an extended period of time. For example, the pure form 1 of (N,N-Diethylcarbamoyl)methyl methyl (2E)but-2-ene-1,4-dioate can be produced by suspending 300 mg (N,N-Diethylcarbamoyl)methyl methyl (2E)but-2-ene-1,4-dioate solid in 1 mL tert-butyl ether (MTBE) at room temperature for 24 hours, followed by vacuum filtration and drying.

Differential Scanning calorimetry (DSC) Analysis

DSC analysis was conducted using a TA Instruments Q2000 DSC equipped with a refrigerated cooling system. For all DSC analyses, 2-5 mg of sample was loaded into $T_{zero}$ aluminum pans with crimpled lids. A pinhole was made at the center of the lid to avoid any pressure buildup during heating. Samples were equilibrated at 10° C. and ramped at a heating rate of 10° C. per minute under a purge of dry nitrogen gas. The data acquisition was controlled by Thermal Advantage software Release 4.9.1. The data were analyzed with Universal Analysis 2000 software (version 4.5A).

The DSC thermogram (FIG. 2) shows that form 1 of (N,N-Diethylcarbamoyl)methyl methyl (2E)but-2-ene-1,4-dioate first melts at about 58° C.

Thermogravimetric Analysis (TGA)

Thermal gravimetric analysis was conducted using a TA Instruments Q5000 thermogravimetric analyzer. For all TGA analyses, 5-10 mg of sample was loaded onto a platinum pan and heated at a rate of 10° C. per minute under a purge of dry nitrogen gas. The data acquisition was controlled by Thermal Advantage software Release 4.9.1. The data was analyzed with Universal Analysis 2000 software (version 4.5A).

The TGA thermogram (FIG. 3) shows that form 1 of N,N-Diethylcarbamoyl)methyl methyl (2E)but-2-ene-1,4-dioate does not undergo any weight loss prior to melting, which indicates that the form 1 is an anhydrous crystalline solid.

X-Ray Powder Diffraction (XRPD) Analysis

Powder X-ray diffraction analysis was performed using a PANalytical X'Pert Pro X-ray diffractometer. The X-ray source was Cu $K_\alpha$ radiation ($\lambda$=1.54051 Å) with output voltage of 45 kV and current of 40 mA. The instrument adopts a para-focusing Bragg-Brentano geometry with incident divergence and scattering slits set at $\frac{1}{16}°$ and $\frac{1}{8}°$ respectively. Large Soller slits (0.04 rad) were used for both incident and diffracted beam to remove axial divergence. A small amount of powder (9-12 mg) was gently pressed onto the single crystal silicon sample holder to form a smooth surface, and samples were subjected to spinning at a rate of two revolutions per second, throughout the acquisition process. The samples were scanned from 2° to 40° in 2θ with a step size of 0.017° and a scan speed of 0.067°/sec. The data acquisition was controlled and analyzed by X'Pert Data Collector (version 2.2d) and X'Pert Data Viewer (version 1.2c), respectively.

The X-ray diffraction pattern for form 1 of the (N,N-Diethylcarbamoyl)methyl methyl (2E)but-2-ene-1,4-dioate is shown in FIG. 1. Unless otherwise specified, the experimental data for X-ray powder diffraction were collected at room temperature.

HPLC Analysis

HPLC analysis is performed using an Agilent HPLC, UV detector monitoring at 210 nm wavelength, and an Inertsil ODS-4 C-18 chromatography column (4.6×150 mm, 3 μm particle size) at 35° C., using an injection volume of a 10 μL sample with an approximate concentration of 0.1 mg/mL. The eluent consists of a 30 minute gradient between two separate mobile phases; mobile phase A consisting of water with 0.05% phosphoric acid and mobile phase B consisting of 90% acetonitrile/10% water/0.05% phosphoric acid at a flow rate of 1 ml/min.

| Time (min) | % Mobile Phase A | % Mobile Phase B |
|---|---|---|
| 0 | 98 | 2 |
| 6 | 65 | 35 |
| 15 | 55 | 45 |
| 25 | 10 | 90 |
| 25.1 | 98 | 2 |
| 30 | 98 | 2 |

Example 2

Synthesis, Purification and Analysis of Crystalline Form 2 of (N,N-Diethylcarbamoyl)methyl methyl (2E)but-2-ene-1,4-dioate Approximately 50 mg of N,N-Diethylcarbamoyl)methyl methyl (2E)but-2-ene-1,4-dioate was dissolved completely in 1 mL isopropanol/water (1/1 v/v), followed by evaporation of solvent in a fume hood. The obtained crystals after solvent evaporation were shown to be pure form 2.

Differential Scanning Calorimetry (DSC) Analysis

DSC analysis was conducted using a TA Instruments Q2000 DSC equipped with a refrigerated cooling system. For all DSC analyses, 2-5 mg of sample was loaded into $T_{zero}$ aluminum pans with crimpled lids. A pinhole was made at the center of the lid to avoid any pressure buildup during heating. Samples were equilibrated at 10° C. and ramped to at a heating rate of 2° C. per minute under a purge of dry nitrogen gas. The data acquisition was controlled by Thermal Advantage software Release 4.9.1. The data were analyzed with Universal Analysis 2000 software (version 4.5A).

The DSC thermogram (FIG. 5) shows that form 2 of (N,N-Diethylcarbamoyl)methyl methyl (2E)but-2-ene-1,4-dioate first melts at about 50° C., followed by recrystallization and melting. The second melting completes at approximately 60° C.

Thermogravimetric Analysis (TGA)

Thermal gravimetric analysis was conducted using a TA Instruments Q5000 thermogravimetric analyzer. For all TGA analyses, 5-10 mg of sample was loaded onto a platinum pan and heated at a rate of 2° C. per minute under a purge of dry nitrogen gas. The data acquisition was controlled by Thermal Advantage software Release 4.9.1. The data was analyzed with Universal Analysis 2000 software (version 4.5A).

The TGA thermogram (FIG. 6) shows that form 2 of (N,N-Diethylcarbamoyl)methyl methyl (2E)but-2-ene-1,4-dioate does not undergo any weight loss prior to melting, which indicates that the form 2 is an anhydrous crystalline solid.

X-Ray Powder Diffraction (XRPD) Analysis

Powder X-ray diffraction analysis was performed using a PANalytical X'Pert Pro X-ray diffractometer. The X-ray source was Cu $K_\alpha$ radiation ($\lambda$=1.54051 Å) with output voltage of 45 kV and current of 40 mA. The instrument adopts a para-focusing Bragg-Brentano geometry with incident divergence and scattering slits set at $\frac{1}{16}°$ and $\frac{1}{8}°$ respectively. Large Soller slits (0.04 rad) were used for both incident and diffracted beam to remove axial divergence. A small amount of powder (9-12 mg) was gently pressed onto the single crystal silicon sample holder to form a smooth surface, and samples were subjected to spinning at a rate of two revolutions per second, throughout the acquisition process. The samples were scanned from 2° to 40° in 2θ with a step size of 0.017° and a scan speed of 0.067°/sec. The data acquisition was controlled and analyzed by X'Pert Data Collector (version 2.2d) and X'Pert Data Viewer (version 1.2c), respectively.

The X-ray diffraction pattern for form 2 of the (N,N-Diethylcarbamoyl)methyl methyl (2E)but-2-ene-1,4-dioate is shown in FIG. 4. Unless otherwise specified, the experimental data for X-ray powder diffraction were collected at room temperature.

HPLC Analysis

HPLC analysis is performed as described in Example 1.

Example 3

Synthesis, Purification and Analysis of Crystalline Form 3 of (N,N-Diethylcarbamoyl)methyl methyl (2E)but-2-ene-1,4-dioate Approximately 420 mg of (N,N-Diethylcarbamoyl) methyl methyl (2E)but-2-ene-1,4-dioate was heated in a scintillation vial to 70° C., at which temperature solid (N,N-Diethylcarbamoyl)methyl methyl (2E)but-2-ene-1,4-dioate completely melted. The molten compound was immediately immersed into liquid nitrogen. The resulting solid was shown to be pure form 3.

Differential Scanning Calorimetry (DSC) Analysis

DSC analysis was conducted using a TA Instruments Q2000 DSC equipped with a refrigerated cooling system. For all DSC analyses, 2-5 mg of sample was loaded into $T_{zero}$ aluminum pans with crimped lids. A pinhole was made at the center of the lid to avoid any pressure buildup during heating. Samples were equilibrated at 10° C. and ramped at a heating rate of 2° C. per minute under a purge of dry nitrogen gas. The data acquisition was controlled by Thermal Advantage software Release 4.9.1. The data were analyzed with Universal Analysis 2000 software (version 4.5A).

The DSC thermogram (FIG. 8) shows that form 3 of (N,N-Diethylcarbamoyl)methyl methyl (2E)but-2-ene-1,4-dioate first melts at about 47° C. The melting is immediately followed by recrystallization and melting. The second melting completes at approximately 60° C.

Thermogravimetric Analysis (TGA)

Thermal gravimetric analysis was conducted using a TA Instruments Q5000 thermogravimetric analyzer. For all TGA analyses, 5-10 mg of sample was loaded onto a platinum pan and heated at a rate of 2° C. per minute under a purge of dry nitrogen gas. The data acquisition was controlled by Thermal Advantage software Release 4.9.1. The data was analyzed with Universal Analysis 2000 software (version 4.5A).

The TGA thermogram (FIG. 9) shows that form 3 of (N,N-Diethylcarbamoyl)methyl methyl (2E)but-2-ene-1,4-dioate does not undergo any weight loss prior to melting, which indicates that the Form 3 is an anhydrous crystalline solid.

X-Ray Powder Diffraction (XRPD) Analysis

Powder X-ray diffraction analysis was performed using a PANalytical X'Pert Pro X-ray diffractometer. The X-ray source was Cu $K_\alpha$ radiation (λ=1.54051 Å) with output voltage of 45 kV and current of 40 mA. The instrument adopts a para-focusing Bragg-Brentano geometry with incident divergence and scattering slits set at 1/16° and 1/8° respectively. Large Soller slits (0.04 rad) were used for both incident and diffracted beam to remove axial divergence. A small amount of powder (9-12 mg) was gently pressed onto the single crystal silicon sample holder to form a smooth surface, and samples were subjected to spinning at a rate of two revolutions per second, throughout the acquisition process. The samples were scanned from 2° to 40° in 2θ with a step size of 0.017° and a scan speed of 0.067°/sec. The data acquisition was controlled and analyzed by X'Pert Data Collector (version 2.2d) and X'Pert Data Viewer (version 1.2c), respectively.

The X-ray diffraction pattern for form 3 of the (N,N-Diethylcarbamoyl)methyl methyl (2E)but-2-ene-1,4-dioate is shown in FIG. 7. Unless otherwise specified, the experimental data for X-ray powder diffraction were collected at room temperature.

HPLC Analysis

HPLC analysis is performed as described in Example 1.

Example 4

Synthesis, Purification and Analysis of Crystalline Form 4 of (N,N-Diethylcarbamoyl)methyl methyl (2E)but-2-ene-1,4-dioate At a temperature of about 50-70° C., under a nitrogen atmosphere, a slurry of mono-methyl fumarate (130 g), toluene (800 mL) and N,N-diethylchloroacetamide (157 g) is added to triethylamine (1.07 g). The temperature is adjusted to 85-95° C. and maintained there for 4 hours. Then the temperature is then adjusted to 15-25° C. and the mixture is subjected to vigorous agitation. After 30 minutes of vigorous agitation in 200 mL of water, the agitation is stopped and the phases are allowed to separate for 30 minutes. The upper organic phase is washed with additional deionized water (75 mL) with vigorous agitation for 30 minutes. The agitation is then stopped and the phases are allowed to separate for 30 minutes. The organic layer is dried over anhydrous sodium sulfate (25 g) for 2 hours. The reaction is filtered and the solution is cooled to 10-20° C. Heptane (1600 mL), at −5 to −20° C. is added over 5 minutes. The reaction is cooled to −5° C. to −10° C. for 24 to 48 hours. The resulting product is air dried for 12 hours. XRPD analysis confirms product is form 4.

Differential Scanning Calorimetry (DSC) Analysis

DSC analysis was conducted using a TA Instruments Q2000 DSC equipped with a refrigerated cooling system. For all DSC analyses, 2-5 mg of sample was loaded into $T_{zero}$ aluminum pans with crimped lids. A pinhole was made at the center of the lid to avoid any pressure buildup during heating. Samples were equilibrated at 10° C. and ramped to a rate of 2° C. per minute under a purge of dry nitrogen gas. The data acquisition was controlled by Thermal Advantage software Release 4.9.1. The data were analyzed with Universal Analysis 2000 software (version 4.5A).

The DSC thermogram (FIG. 11) shows that form 4 of (N,N-Diethylcarbamoyl)methyl methyl (2E)but-2-ene-1,4-dioate undergoes a solid-solid phase transformation at approximately 38° C. The resulting solid melts at approximately 58° C.

Thermogravimetric Analysis (TGA)

Thermal gravimetric analysis was conducted using a TA Instruments Q5000 thermogravimetric analyzer. For all TGA analyses, 5-10 mg of sample was loaded onto a platinum pan and heated at a rate of 2° C. per minute under a purge of dry nitrogen gas. The data acquisition was controlled by Thermal Advantage software Release 4.9.1. The data was analyzed with Universal Analysis 2000 software (version 4.5A).

The TGA thermogram (FIG. 12) shows that form 4 of (N,N-Diethylcarbamoyl)methyl methyl (2E)but-2-ene-1,4-dioate does not undergo any weight loss prior to melting, which indicates that the form 4 is an anhydrous crystalline solid.

X-Ray Powder Diffraction (XRPD) Analysis

Powder X-ray diffraction analysis was performed using a PANalytical X'Pert Pro X-ray diffractometer. The X-ray source was Cu $K_\alpha$ radiation ($\lambda$=1.54051 Å) with output voltage of 45 kV and current of 40 mA. The instrument adopts a para-focusing Bragg-Brentano geometry with incident divergence and scattering slits set at 1/16° and 1/8° respectively. Large Soller slits (0.04 rad) were used for both incident and diffracted beam to remove axial divergence. A small amount of powder (9-12 mg) was gently pressed onto the single crystal silicon sample holder to form a smooth surface, and samples were subjected to spinning at a rate of two revolutions per second, throughout the acquisition process. The samples were scanned from 2° to 40° in 2θ with a step size of 0.017° and a scan speed of 0.067°/sec. The data acquisition was controlled and analyzed by X'Pert Data Collector (version 2.2d) and X'Pert Data Viewer (version 1.2c), respectively.

The X-ray diffraction pattern for form 4 of the (N,N-Diethylcarbamoyl)methyl methyl (2E)but-2-ene-1,4-dioate is shown in FIG. 10. Unless otherwise specified, the experimental data for X-ray powder diffraction were collected at room temperature.

HPLC Analysis

HPLC analysis is performed as described in Example 1.

What is claimed is:

1. A method of making a pharmaceutical formulation comprising combining
    crystalline N,N-Diethylcarbamoyl)methyl methyl (2E)but-2-ene-1,4-dioate exhibiting characteristic scattering angles (2θ) at least at 14.5±0.2°, 21.7±0.2°, 12.3±0.2°, 29.0±0.2°, and 27.1±0.2° in an X-ray powder diffraction pattern measured using Cu—$K_\alpha$ radiation, the crystalline N,N-Diethylcarbamoyl)methyl methyl (2E)but-2-ene-1,4-dioate having a purity of at least 99% by weight as measured by HPLC; and
    a pharmaceutically acceptable vehicle.

2. The method of claim 1, wherein the crystalline N,N-Diethylcarbamoyl)methyl methyl (2E)but-2-ene-1,4-dioate has a DSC thermogram peak of between about 57° C. and about 59° C.

3. The method of claim 1, wherein the crystalline N,N-Diethylcarbamoyl)methyl methyl (2E)but-2-ene-1,4-dioate further exhibits characteristic scattering angles (2θ) at least at 21.0±0.2°, 22.8±0.2°, 19.8±0.2°, 6.8±0.2°, and 20.3±0.2° in an X-ray powder diffraction pattern measured using Cu—$K_\alpha$ radiation.

4. The method of claim 1, wherein the crystalline N,N-Diethylcarbamoyl)methyl methyl (2E)but-2-ene-1,4-dioate exhibits characteristic scattering angles (2θ) in an X-ray powder diffraction pattern measured using Cu—$K_\alpha$ radiation shown in FIG. 1.

5. The method of claim 1, wherein the crystalline N,N-Diethylcarbamoyl)methyl methyl (2E)but-2-ene-1,4-dioate has a purity of at least 99.5% by weight as measured by HPLC.

6. The method of claim 1, wherein the crystalline N,N-Diethylcarbamoyl)methyl methyl (2E)but-2-ene-1,4-dioate has a purity of at least 99.9% by weight as measured by HPLC.

7. The method of claim 1, wherein the pharmaceutically acceptable vehicle comprises a diluent, a pharmaceutically acceptable adjuvant, a pharmaceutically acceptable excipient, a pharmaceutically acceptable carrier, or a combination of any of the foregoing.

8. The method of claim 7, wherein the pharmaceutically acceptable vehicle comprises sodium citrate, dicalcium phosphate, or a combination thereof.

9. The method of claim 1, wherein the pharmaceutically acceptable vehicle comprises starches, lactose, sucrose, glucose, mannitol, silicic acid, carboxymethylcellulose, alginates, gelatin, polyvinylpyrrolidinone, sucrose, acacia, glycerol, gar-agar, calcium carbonate, potato starch, tapioca starch, alginic acid, certain silicates, sodium carbonate, paraffin, quaternary ammonium compounds, cetyl alcohol, glycerol monostearate, kaolin, bentonite clay, talc, calcium stearate, magnesium stearate, solid polyethylene glycols, sodium lauryl sulfate, or a combination of any of the foregoing.

10. The method of claim 1, wherein the pharmaceutical formulation is an oral dosage form.

11. A method of treating a disease in a patient in need thereof, comprising administering to the patient a therapeutically effective amount of the pharmaceutical formulation of claim 1, wherein the disease is selected from selected from multiple sclerosis and psoriasis.

* * * * *